(12) United States Patent
Chen et al.

(10) Patent No.: US 12,246,176 B1
(45) Date of Patent: Mar. 11, 2025

(54) SYSTEM AND METHOD FOR THE ACTIVATION OF ACTIVE ION TRANSPORTERS WITHOUT THE CONSUMPTION OF ADENOSINE TRIPHOSPHATE (ATP) MOLECULES FOR THE TREATMENT OF LIMB ISCHEMIA

(71) Applicant: WR Biotech, LLC, Tampa, FL (US)

(72) Inventors: Wei Chen, Tampa, FL (US); Ruisheng Liu, Tampa, FL (US)

(73) Assignee: WR Biotech, LLC, Tampa, FL (US)

( * ) Notice: Subject to any disclaimer, the term of this patent is extended or adjusted under 35 U.S.C. 154(b) by 252 days.

(21) Appl. No.: 18/185,523

(22) Filed: Mar. 17, 2023

Related U.S. Application Data

(60) Provisional application No. 63/320,947, filed on Mar. 17, 2022.

(51) Int. Cl.
   *A61N 1/36* (2006.01)
   *A61N 1/04* (2006.01)
   *A61N 1/32* (2006.01)

(52) U.S. Cl.
   CPC ......... *A61N 1/36034* (2017.08); *A61N 1/323* (2013.01); *A61N 1/0408* (2013.01); *A61N 1/0476* (2013.01)

(58) Field of Classification Search
   None
   See application file for complete search history.

(56) References Cited

U.S. PATENT DOCUMENTS

| | | | |
|---|---|---|---|
| 4,165,750 | A | 8/1979 | Aleev et al. |
| 8,073,549 | B2 | 12/2011 | Chen |
| 2010/0249757 | A1* | 9/2010 | Chen .................. A61N 1/32 |
| | | | 604/890.1 |

OTHER PUBLICATIONS

Tran et al., "Synchronization Modulation Increases Transepithelial Potentials in MDCK Monolayers through Na/K Pumps," Apr. 2013.PLOS one, pp. 1-9.

Jeon et al., "Effects of Pulse Duration on Muscle Fatigue During Electrical Stimulation Inducing Moderate-Level Contraction," Muscle & Nerve. Apr. 2018, pp. 1-8.

Mckenna et al., "Muscle K+, Na+, and Cl—disturbances and Na+-K+ pump inactivation: implications for fatigue," J Appl Physiol. Oct. 2007.

(Continued)

*Primary Examiner* — Michael W Kahelin
(74) *Attorney, Agent, or Firm* — Molly L. Sauter; Smith & Hopen, P.A.

(57) ABSTRACT

A system and method for treatment of ischemia limb by operating the sodium-potassium (Na/K) pumps of the ischemia limb to consume one ATP to actively extrude 3 Na⁺ and pumping in 2 K⁺ ions, synchronizing the Na/K pump molecules down to individual steps in a pumping cycle and then switching to a noncanonical mode to synthesize one ATP molecule at end of each pumping cycle. The synthesis of ATP molecule compensates the ATP consumed in actively transporting ions. As a result, the zero-consumption of ATP for the electrically modulated Na/K pumps controlled by the system and method of the present invention save the residual limited ATP molecules in the ischemia limb to maintain the living environment of the cells in the ischemia limb, and therefore recover the functions of the limb.

20 Claims, 17 Drawing Sheets

(56) References Cited

OTHER PUBLICATIONS

Liang, "The modified Synchronization Modulation technique revealed mechanisms of Na,K-ATPase," ProQuest, Mar. 2019. pp. 1-103.
Dreibati et al., "Influence of electrical stimulation frequency on skeletal muscle force and fatigue," Annals of Physical and Rehabilitation Medicine 53. Jan. 2010, pp. 1-12.
Chen et al., "Electrical Activation of Na/K Pumps Can Increase Ionic Concentration Gradient and Membrane Resting Potential," J. Membrane Biol. 2007, pp. 1-9.
Taghian et al., "Modulation of cell function by electric field: a high-resolution analysis," The Royal Society. Apr. 2015, pp. 1-11.
Liu et al., "Activation of Na+ and K+ pumping modes of (Na, K)-ATPase by an Oscillating Electric Field," The Journal of Biological Chemistry vol. 265, No. 13, May 1990.
Di et al., "Effects of power frequency electric field exposure on kidney," Ecotoxicology and Environmental Safety. Feb. 2020, pp. 1-7.
Blank, "Na,K-ATPase function in alternating electric fields," The FASEB Journal vol. $ Mar. 2020. pp. 1-5.

* cited by examiner

SYSTEM AND METHOD FOR THE ACTIVATION OF ACTIVE ION TRANSPORTERS WITHOUT THE CONSUMPTION OF ADENOSINE TRIPHOSPHATE (ATP) MOLECULES FOR THE TREATMENT OF LIMB ISCHEMIA

CROSS-REFERENCE TO RELATED APPLICATIONS

This application claims priority to U.S. Provisional Patent Application No. 63/320,947 filed on Mar. 17, 2022 and entitled "System and Method for the Activation of Active Ion Transporters without the Consumption of Adenosine Triphosphate (ATP) Molecules for the Treatment of Acute Limb Ischemia and for Protection of a Donor Heart for Transplantation", the entirety of which is incorporated herein by reference.

BACKGROUND OF THE INVENTION

In daily life, limb ischemia often occurs, especially for workers and soldiers. Placing heavy materials on limbs or pressure on the blood vessels over a long period of time will inevitably reduce blood flow and the ability to deliver nutrition and oxygen to muscle cells, resulting in the limb ischemia. If the blood flow is not quickly resumed, dysfunction of the limb may occur. Sometimes, functions of the limb may be permanently lost. Treatments to save the ischemia limb, to prevent damage or to recover the limb functions are topics in today's medicine.

In muscle cells, except muscle contraction, there are many membrane proteins consuming energy, such as various electrogenic pumps and different kinds of secondary active exchangers, where the Na/K pump, or Na/K ATPase is the major ATP consumer.

Na/K pump is one of the most prevalent active membrane transporters in almost all kinds of cells. Na/K pump extrudes three Na ions out of the cell via the exchange of two K ions by consuming one adenosine 5'-triphosphate (ATP) in each pumping cycle to maintain the ionic concentration gradients and the membrane potential difference. Na/K pump is a unique energy converter converting the organic ATP hydrolysis energy to the inorganic electrochemical potential difference across the cell membrane so that many other membrane proteins can easily utilize the energy.

In order to prevent damage to the ischemia limb or quickly and maximally recover the functions of the limb, the functions of the Na/K pumps in the ischemia limb, regardless of the lack of ATP molecules, must be maintained.

Accordingly, what is needed in the art is a system and method that maintains the pumping function of the Na/K pumps that can be used for the treatment and recovery of limb ischemia.

SUMMARY OF THE INVENTION

In various embodiments, the present invention, application of the $3^{rd}$ generation synchronization modulation technique ($3^{rd}$-SMEF) to the ischemia limbs provides a system and method to not only save the residual limited ATP molecules by using electric energy to fuel the pumping cycle but also keep the functions of the Na/K pumps to maintain the functions of the ischemia limb.

In one embodiment, a method for controlling Na/K pump molecules for the treatment of limb ischemia is provided. The method includes, applying an oscillating electric field to an ischemia limb comprising Na/K pump molecules, wherein the oscillating electric field comprises three serially applied phases and wherein applying the oscillating electric field comprises and applying a synchronization phase to synchronize the Na/K pump molecules down to individual steps within a running cycle at an Na/K pump molecule physiological turnover rate with a net-consumption of adenosine triphosphate (ATP) substantially equal to zero. The method further includes, applying a modulation phase to up modulate the synchronized Na/K pump molecules to a predetermined target turnover rate and applying a maintenance phase to maintain the synchronized Na/K pump molecules at the predetermined target turnover rate for a predetermined duration of time.

In another embodiment, a system for controlling Na/K pump molecules for the treatment of limb ischemia is provided. The system includes, an electric field generator to generate an oscillating electric field, a first pair of electrodes and a second pair of electrodes to simultaneously apply the oscillating electric field to an ischemia limb comprising Na/K pump molecules, wherein the first pair of electrodes and the second pair of electrodes are positioned perpendicular to each other on the surface of the ischemia limb, wherein the first pair of electrodes and the second pair of electrodes are independent and wherein the oscillating electric field comprises three serially applied phases. Applying the oscillating electric field additionally includes, applying a synchronization phase to synchronize the Na/K pump molecules down to individual steps within a running cycle at an Na/K pump molecule physiological turnover rate with a net-consumption of adenosine triphosphate (ATP) substantially equal to zero, applying a modulation phase to up modulate the synchronized Na/K pump molecules to a predetermined target turnover rate and applying a maintenance phase to maintain the synchronized Na/K pump molecules at the predetermined target turnover rate for a predetermined duration of time.

In an additional embodiment, a computer-readable medium storing a set of instructions configured for being executed by at least one processor for performing a method for controlling Na/K pump molecules for the treatment of limb ischemia is provided. The instructions for the performed method include, controlling an electric field generator to apply an oscillating electric field to an ischemia limb comprising Na/K pump molecules, wherein the oscillating electric field comprises three serially applied phases. Applying the oscillating electric field further includes, applying a synchronization phase to synchronize the Na/K pump molecules down to individual steps within a running cycle at an Na/K pump molecule physiological turnover rate with a net-consumption of adenosine triphosphate (ATP) substantially equal to zero, applying a modulation phase to up modulate the synchronized Na/K pump molecules to a predetermined target turnover rate and applying a maintenance phase to maintain the synchronized Na/K pump molecules at the predetermined target turnover rate for a predetermined duration of time.

In a various embodiments, the present invention provides a system and method for synchronizing the Na/K pumps, down to individual steps in the running cycle and driving the active ion transports in the physiological running conditions to actively transport ions across the cell membrane by consuming one ATP, and simultaneously injecting electric energy to the transporter to synthesize one ATP for each running cycle. As a result, the generated ATP molecules compensate the ATP consumed in actively transporting ions across the cell membrane. The net ATP consumption of the electrically synchronized Na/K pumps is significantly reduced, theoretically to zero, and then, gradually modulate the Na/K pumps or increase the pumping rate to a pre-determined turnover rate by progressively increasing the synchronization frequency of the Na/K pumps in a stepwise pattern.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE INVENTION

Figure 1A:
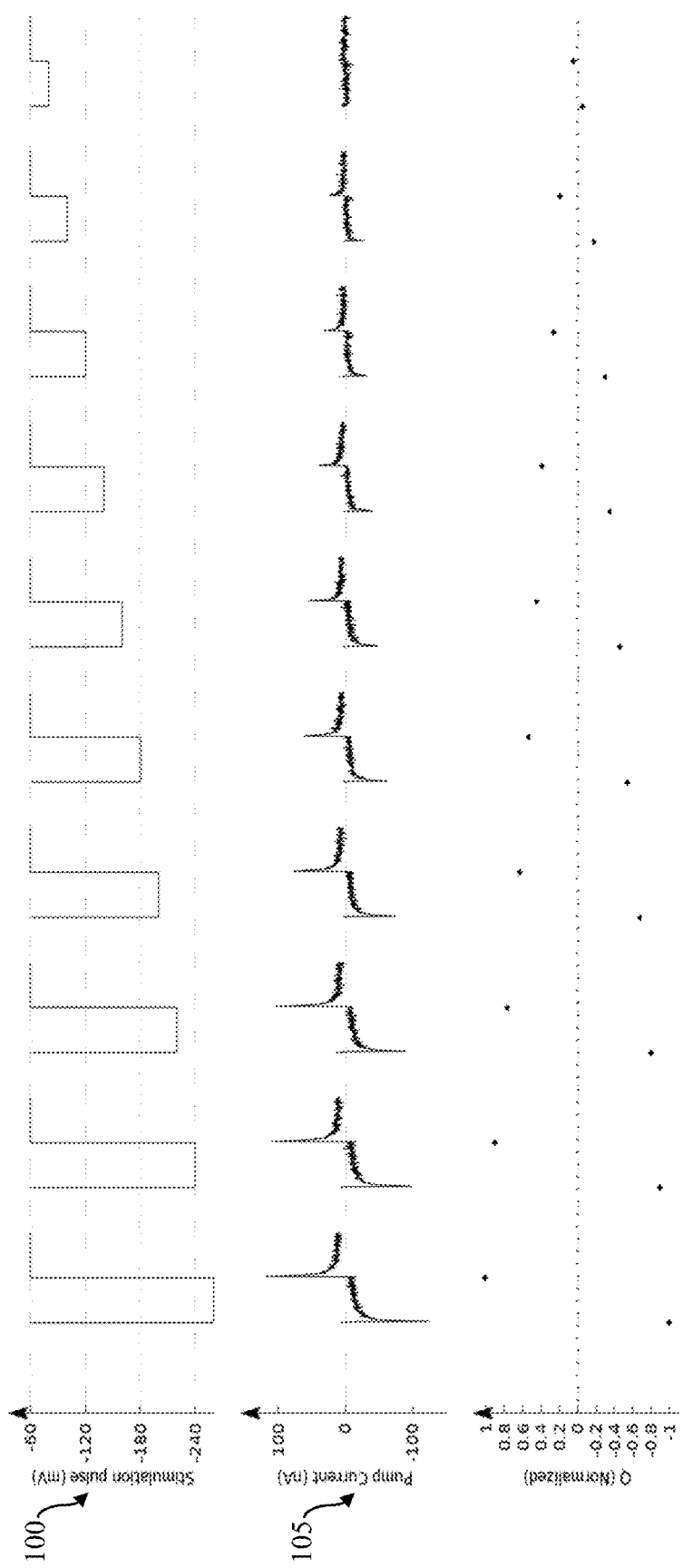
FIG. 1A illustrates pump currents measured from the dialyzed pump molecules in the absence of ATP molecules with an extra-cellular K concentration of 8 mM.

In various embodiments, the present invention provides a method to recover the functions of the ischemia limb by applying the $3^{rd}$ generation synchronization modulation electric field which not only maintains and activates the Na/K pumps to a specific pumping rate to compensate the ischemia effects, but also uses electric energy to substitute ATP hydrolysis energy in fueling the pumping cycle. As a result, the ischemia limb can be quickly recovered regardless of the reduced ATP molecules.

Previously, a $2^{nd}$ generation synchronization modulation technique successfully measured the real-time semi-single pump currents in both the dialyzed and physiological running pump molecules. The transient pump currents with extremely short time course (less than 100 μs) as short as the membrane capacitance currents confirmed the free and kinetical movements of the ions along the channel-like structures. The transient pump currents represent the power-stroke in the pumping cycle which proved the free movements of the ions along the channel-like structures without protein conformational change in the transmembrane domain. Moreover, these free ion-movements along the channel-like structure indicate that one will be able to electrically inject electric energy to the pumps to manipulate the pump functions by acceleration of the ion-movements.

The $2^{nd}$ generation synchronization modulation technique further allowed one to measure the real-time semi-single pump currents from the non-canonical pump model, such as the Na/Na exchange mode, where the same amount of the ions is transported across the cell membrane without ATP consumption. Again, the transient, separated inward and outward pump currents show the extremely short time course, as short as the membrane capacitance currents with the same magnitude. The transient pump currents, especially the inward pump currents as transient as the outward pump currents with the same magnitude indicate that the ATP hydrolysis energy drives the Na ions kinetically moving out of the cell to build up an ionic concentration gradient, and then, the potential energy is fully converted to the kinetic energy of the downhill Na ions moving into the cell. Based on the energy conservation law, hydrolysis of one ATP molecule release 550 meV energy, synthesis of one ATP molecule requires at least the same amount of energy.

Therefore, the kinetic energy carried by the downhill Na ions must be the driving force for the ATP synthesis, and the site of ATP synthesis must be in the intracellular loop domain.

By utilizing the dual energy-convert features of the Na/K pumps in the physiological running mode and the non-canonical pumping mode, and by introducing the concept of electronic synchrotron accelerator in physics to the biological system, a $3^{rd}$ generation synchronization modulation electric field is disclosed that can use electric energy to substitute ATP hydrolysis energy in fueling the pumping cycle. Briefly, the pump first consumes ATP hydrolysis energy to transport 3 Na and 2 K ions against the electrochemical potential difference to build up ionic concentration gradients, where the electric field is used to inject energy to the pumps by accelerating the ion movements, Then, switching to the non-canonical pumping mode, the kinetic energy of 2 K ions is used to synthesize ATP. As a result, there is no net ATP consumption in the pumping cycle actively transporting 3 Na and 2 K ions, or electric energy is used to substitute ATP hydrolysis energy to fuel the pumping cycle to build up ionic concentration gradient across the ionic concentration gradient.

In the following detailed description, the underlying mechanisms involved in development of the $3^{rd}$ generation synchronization modulation electric field of the Na/K pumps is presented based on the dynamics of the pump molecules. The parameters of electric field including the detailed waveform, magnitude and duration for the energy trap, activation overshoot, and plateau, initial and final frequency as well as the step-change are specially designed for the ischemia limb. The design not only effectively controls the pump functions but also avoids side effects on other membrane proteins to maintain activity of the ischemia limb. The 2-dimensional electrode array is developed based on the structure, orientation, dimension of limb. The purpose of the invention is to maximally activate functions of the Na/K pumps to recover the functions of the ischemia limb.

Na/K ATPases, or Na/K pump, is a prevalent active transporter in almost all kinds of cells. In operation, the pump extrudes 3 Na ions by exchanging 2 K ions to build up Na and K concentration gradients and the potential difference across the cell membrane, thereby providing the critical environment for living cells. The pump generated electrochemical potential difference across the cell membrane, including ionic concentration gradient and the membrane potential difference, are the energy source for many voltage-dependent membrane proteins. For example, various voltage-dependent or voltage-gated ion channels utilize the membrane potential to generate action potentials and propagate the action potentials along the cell membrane. Another example are Na/H exchangers, that influence pH value. The ionic concentration gradients also play a significant role in controlling the cell volume and homeostasis. Therefore, electrical activation of the Na/K pumps to a specific value regardless of the reduced ATP concentration to maintain the necessary ionic concentration gradient and the potential difference across the cell membrane, or the cell living environment, is critical to the ischemia limb.

Na/K pump is a unique energy converter that transfers the organic ATP hydrolysis energy to the inorganic energy, electrochemical potentials across the cell membrane to provide energy for many membrane proteins including ion-channels, various pump molecules, and secondary active transporters.

In the pumping cycle, to be able to transport ions across the cell membrane against the concentration gradients, the pump functions must be sensitive to the membrane potential. In fact, large efforts have been previously made in the past to electrically activate the pump functions. In the early 1980's, previous works first showed that the kilo- and mega-Hz oscillating electric field can activate the Na- and K-transports, respectively for about 30%. Later, many models were developed to explain the possible mechanisms in electrical activation of the pump molecules including resonance, Brownian motor, electronic transition, thermal noise, adiabatic process, and so on. However, no practical technique is known that can effectively control the Na/K pumps, not to mention saving ATP molecules.

In order to use electric energy to substitute ATP hydrolysis energy in fueling the Na/K pumps, one must understand the mechanisms, especially the dynamics in the pumping cycle, or how the ATP hydrolysis energy drives the pumping cycle in actively transporting Na and K ions.

Since discovered in 1950s, Na/K pumps have been well studied. Based on the Pos-Albert model, the pumping cycle consists of a series of stochastic biochemical reactions through a random walk. The pumping cycle reaches the thermodynamic equilibrium without power-stroke in the pumping cycle. The protein conformational changes between E1 and E2 transport 3 Na and 2 K ions across the cell membrane. One of the pieces of evidence is that the measured pump currents show the small, static, net-outward currents.

Later, a two-access-channel model was developed which allocates the protein conformational changes deeply inside the cell membrane, so called the "binding pocket", sandwiched by two access channels connecting the internal and external solution. The evidence comes from the study of the dialyzed pumps where all the Na ions (both the internal and external) were eliminated so that the pump molecules can only react with K ions. The results showed that a negative electric stimulation pulse can generate forward pump currents. Once the stimulation is over, the backward pump currents with the same value and time course as the forward pump currents were generated. These are typical features of the displacement current, indicating that the channel-like structure is somehow blocked deeply in the cell membrane.

Currently, little is known about the dynamics of the pumping cycle, i.e., how the ATP hydrolysis energy released in the cytoplasmic loop drives the pumping cycle and generating the protein conformational change to active transport Na and K ions.

To better understand the dynamics of the Na/K pumps for the development of the present invention, energy analyses were conducted for the pumping cycle based on the Energy Conservation Law. The Na and K concentration gradients across the cell membrane are equivalent to the potential difference of Na and K ions as +60 mV and −90 mV, respectively. It is well-known that Na/K pump has a wide range of the membrane potentials, about ±100 mV with respective to the membrane resting potential at about-90 mV. At the membrane potential of −123.3 mV, which is in the range of pump running potentials, the energy required to extrude 3 Na ions is about 550 meV (=3e (123.3+60) mV), the same as the energy released from hydrolysis of one ATP molecule. All the ATP hydrolysis energy must be used to drive out 3 Na ions against the potential difference. No energy is left for the protein conformation change. This simple but fundamental energy analysis suggests that ion-movements across the cell membrane cannot be achieved by the protein conformational changes. ATP hydrolysis energy must somehow directly drive 3 Na ions out of the cells against the potential difference, and therefore, Na/K pump should have a channel-like structure in the transmembrane domain. This is similar as to send a ball to the top of a building with minimum energy, the best way is the kick up the ball.

This is consistent with the previous energetic studies of the ATP hydrolysis. ATP hydrolysis energy is not released when the chemical bond is broken from ATP to ADP*Pi, but at the time the inorganic y-phosphate (Pi) is repelled by the electrostatic force physically moving away from ADP outside the ATPase active sites. ATP hydrolysis energy is converted to the kinetic energy carried by the cleaved Pi. The biochemical ATP hydrolysis energy is converted to the kinetic energy of Pi to drive Na-transport, which is further transferred as the kinetical energy of 3 Na ions freely moving against the electrochemical potential difference through the channel-like structure.

The channel-like structure hypothesis is consistent with the previous studies of channel configuration. The PTX-treated pump molecules from previous work exhibit the channel functions allowing ions passing through. Previous studies of the reactivity of each amino acid in different transmembrane helices using the substituted cysteine accessibility method (SCAM) revealed a single unbroken cation pathway through the pump-channel.

As a result, Na/K pump should have separated, transient outward Na and inward K currents. Due to the free and kinetical movements of the ions along the channel-like structure, the moving speed must be fast in order to have enough energy to overcome the potential difference. Therefore, the time required for ions to move across the cell membrane should be extremely short showing transient pump currents. Due to the Na and K ions sequentially moving across the cell membrane, Na- and K-pump currents must be separated. All these are different from the measured pump currents showing the static, net-outward currents.

Figure 1B:
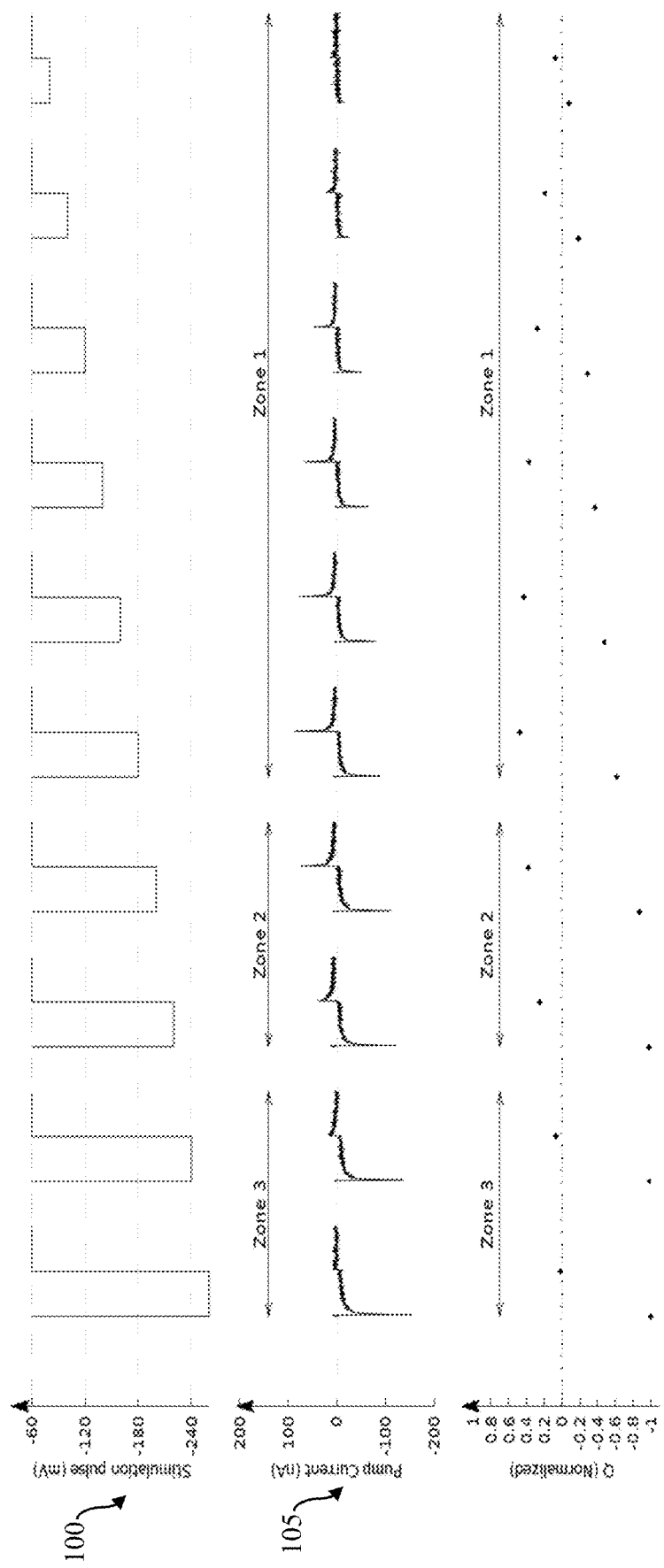
FIG. 1B illustrates pump currents measure from the dialyzed pump molecules in the absence of ATP molecules with an extra-cellular K concentration of 40 mM.
Figure 1C:
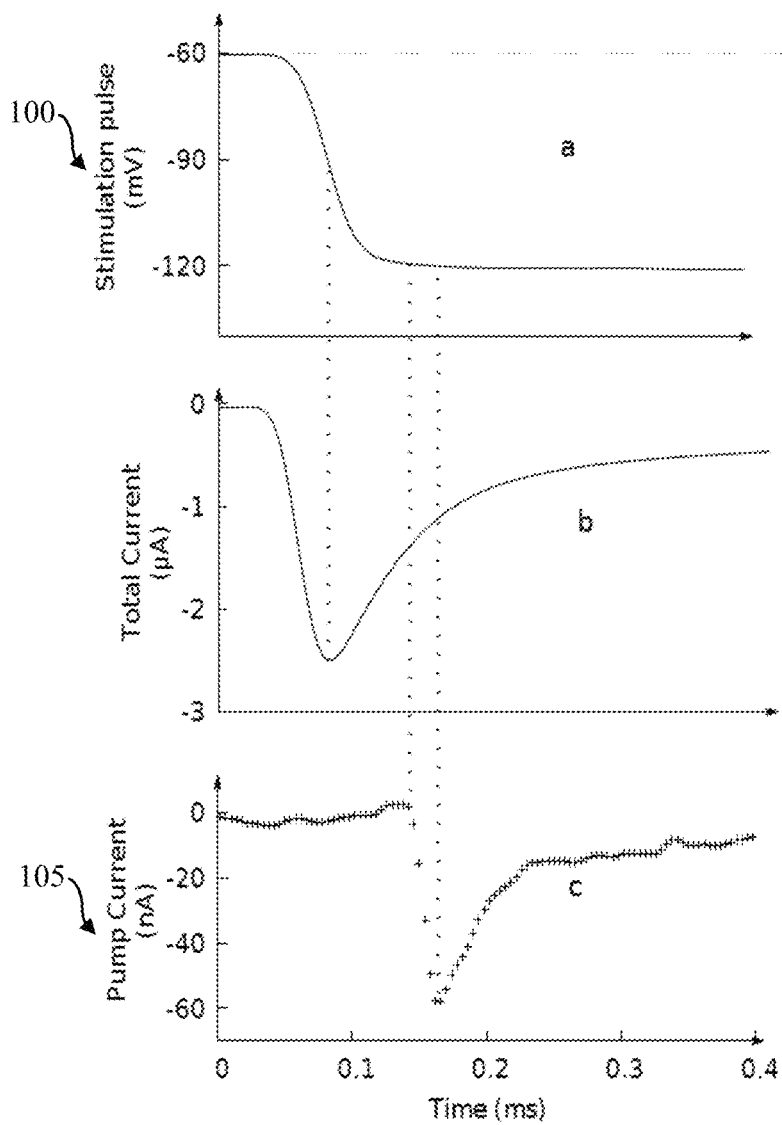
FIG. 1C illustrates the stimulation pulse, the corresponding total transmembrane current and the transient pump currents.

FIG. 1A-FIG. 1C illustrate the pump currents measured from the dialyzed pump molecules. Na ions in both the internal and external solutions are fully eliminated, and ATP concentration was significantly reduced by at least five times washout. Upper traces in both FIG. 1A and FIG. 1B show a series of stimulation pulses from −20 to −200 mV at the holding potential of −60 mV. Middle traces in both FIG. 1A and FIG. 1B show the generated pump currents. For FIG. 1A, the intra- and extra-cellular K concentration was 140 and 8 mM, respectively, as the previous studies. The stimulation pulse drives the forward pump current indicating K ions moving into the protein. Once the stimulation pulse was over, the backward pump current was generated with the same magnitude and time course, representing the ions moving back out of the pump molecules, or the channel-like structure is blocked deeply inside the cell membrane. The results are the same as those obtained in previous studies. The displacement features of the pump currents are considered as the evidence of the extracellular access-channel in the two-access-channel model.

As shown in FIG. 1B, only the extracellular K concentrations is increased to 40 mM which is still much lower than the intracellular K concentration. The same stimulation pulses generated uni-directional inward transmembrane pump currents.

FIG. 1C illustrates the stimulation pulse, the corresponding total transmembrane (mainly capacitance) current, and the transient pump currents at the same timescale. Duration of all the two-way displacement currents and the uni-direction transmembrane pump currents have the same time course of about 100 us as the membrane capacitance currents. The results suggest that no protein conformational change is involved in the ion movement in the pump molecules.

As shown in FIG. 1A-FIG. 1C, for the dialyzed pump molecules, a stimulation pulse 100 can generate uni-directional transmembrane pump currents 105. Duration of the pump currents is extremely short, similar to the membrane capacitance currents. These results illustrate the free movements of the K ions into the cell. Since this movement happens without ATP molecules, the moving-in K ions are not achieved by the protein conformational changes.

The static, net-outward pump currents measured from the physiology running condition, is a result of the non-stop running of pump molecules. In contrast to the voltage-gate ion-channels being all open at the same time responding to the membrane potential changes, Na/K pumps exhibit a random pumping pace and different pumping rates. Details of the pump currents will be inevitably merged into the current summation. To observe the details of the pump currents, the development of the present invention began to synchronize the pump molecules. For a first-generation synchronization modulation electric field, the pump molecules were synchronized to the Na- and K-transports, therefore, showing the separated outward Na and inward K pump currents but having static values. Later, the technique was improvised as the $2^{nd}$ generation which is effective in synchronizing the pump molecules down to the individual steps, resulting in the real-time, semi-single pump currents.

Due to the opposite voltage-dependence, the field in the positive half-cycle facilitates the Na-transport but hinders the K-transport, so that the positive half-pulses are the Na-transport favorite half-pulse and K-transport unfavorite half-pulse. The negative half-pulse activates K-transport but deactivates the Na-transport so that they are the K-transport favorite half-pulse and the Na-transport unfavorite half-cycle. As the field 100 is oscillating, Na-transports from all the pump molecules will eventually fall into the positive half-cycle, and the K-transports will eventually fall into the negative half-cycle, respectively. Consequently, all the pump molecules run at the same pumping rate as the frequency of the oscillating electric field 100.

The oscillating electric field 100 has a symmetric waveform which can effectively synchronize all the pump molecules in two hemispheres. The field-induced membrane potentials on two hemispheres are always opposite. Any membrane potential change will facilitate the pump molecules in one hemisphere but inevitably hinder the pump molecules in another hemisphere. Under the symmetric oscillating electric field, pump molecules in the two hemispheres can be synchronized into two groups with 180 phase-shift. In other words, the electric field in one half-cycle facilitates the Na-transport of the pump molecules in one hemisphere and activates the K-transport of the pumps in the other hemisphere, and vice versa in another half-cycle. As a result, all the pump molecules in the two hemispheres are synchronized to the same pumping cycle.

Figure 2A:
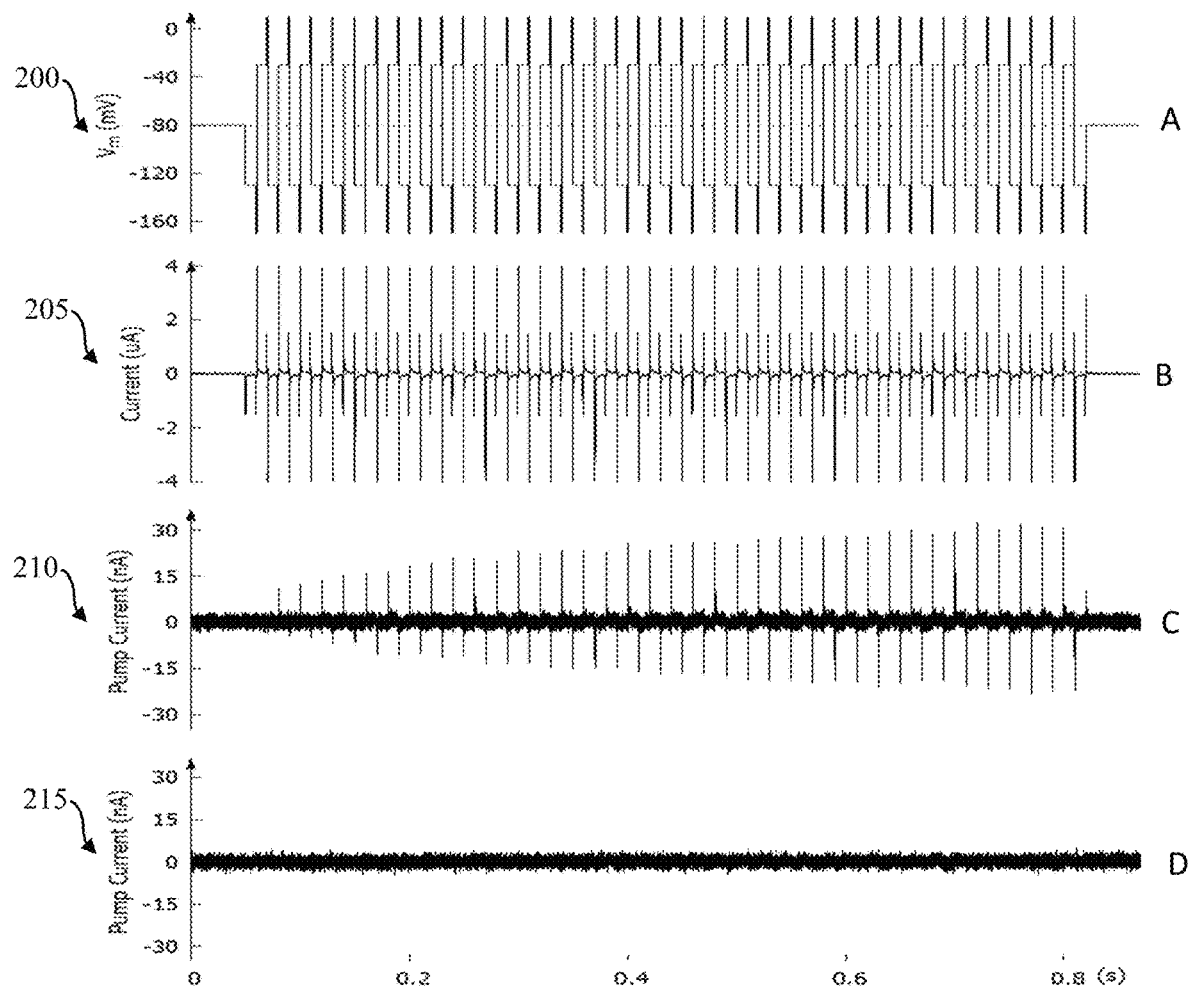
FIG. 2A illustrates pump currents measured from the physiological running condition showing the real-time, semi-single pump currents having the transient, separated outward Na and inward K currents with extremely short time course.

FIG. 2A illustrates 39 oscillating pulses 200 from the $2^{nd}$ generation synchronization electric field. To identify the pump currents, a pre-pulse (not shown) with the same waveform of the oscillating electric field was also applied to the cell membrane. The induced currents 205 function as a template current to be subtracted from the currents generated by each individual oscillating pulses 210 (in μA). The difference is the synchronized pump currents 215 (in nA).

As shown in FIG. 2A, for the first a few oscillating pulses 200, there are no transient pump currents 210 at all because the pump molecules remain randomly paced. As more and more of the Na/K pumps are synchronized, the separated transient outward Na and inward K currents are generated responding to the start of the activation overshoots, and gradually increased until saturation. The magnitude of the transient pump currents 210 is much (tens times) larger than the net outward pump currents measured from the random paced pumps. The outward Na currents over the inward K currents is about 3:2, reflecting the stoichiometric ratio of Na/K pumps. Both the outward and inward pump currents are transient with the time course about 100 μs, the same as the membrane capacitance currents.

Figure 2B:
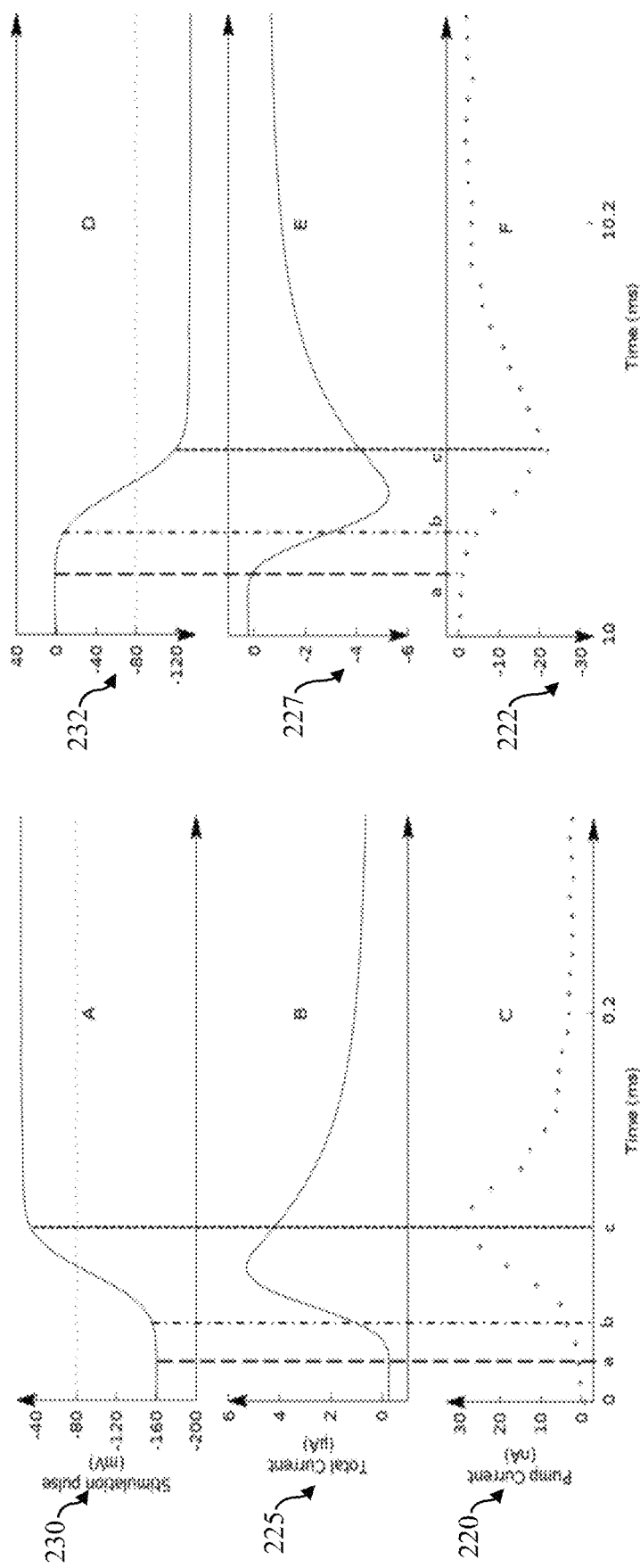
FIG. 2B illustrates the pump currents of FIG. 2A in greater detail.

The transient pump currents 220, 222 are shown in more detail in FIG. 2B with the total transmembrane currents 225, 227 (mainly the capacitance currents) and the membrane potential changes 230, 232 in the same coordinate. Both the membrane capacitance currents 225, 227, and the Na and K pump currents 220, 222 are restricted to the rising phase of the half-pulses having the similar duration.

The transient pump currents 220, 222 with the same time course as the membrane capacitance currents 225, 227 further prove that the ions move across the cell membrane without protein conformational change involved, or the Na/K pump has a channel-like structure.

As shown in FIG. 2A and FIG. 2B, the pump molecules at physiological running condition generate the transient outward Na and inward K pump currents having the extremely short time course, as short as the membrane capacitance currents. To confirm that pump currents and the membrane capacitance currents have a similar duration, the gain of voltage-clamp was intentionally increased or decreased to shorten or elongate the duration of transmembrane (mainly the capacitance) currents. Regardless of the changes in the gain, it was shown that the pump currents and the membrane capacitance currents always have the similar duration. The results indicate that the Na and K ions freely and kinetically move across the cell membrane through a channel-like structure in the Na/K pumps.

Figure 3:
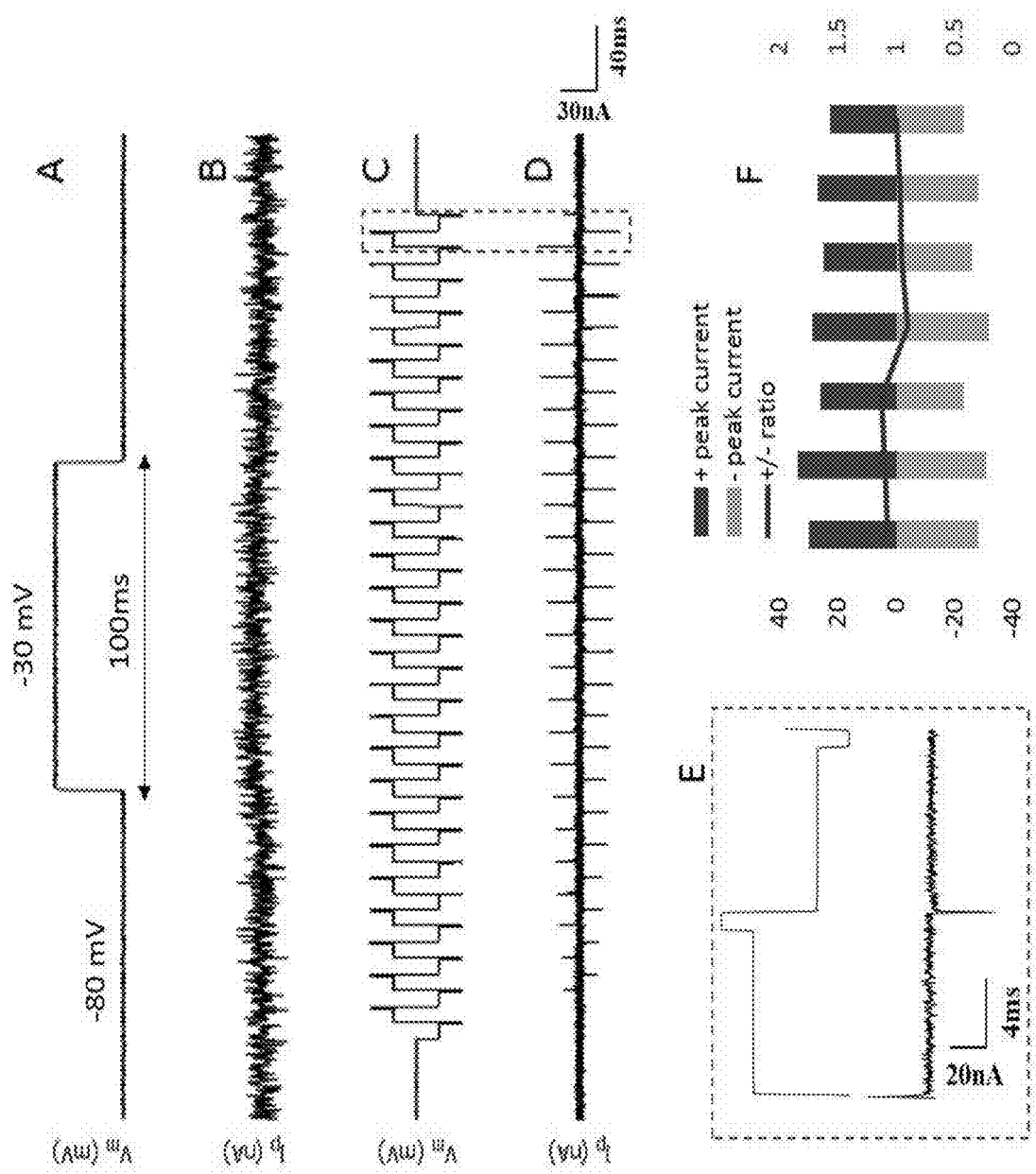
FIG. 3 illustrates the real-time, semi-single pump currents measured from the non-canonical Na/Na exchange mode. The transient inward pump currents with the same magnitude and duration as the outward pump currents indicate that potential energy across the cell membrane is converted to the kinetic energy carrying by the downhill inward Na ions moving into the cell to facilitate ATP synthesis.

FIG. 3 illustrates the real-time, semi-single pump currents measured from the non-canonical Na/Na exchange mode. The outward and inward pump currents have the same magnitude and time course, which is as short as the membrane capacitance currents, which indicates that the inward Na ions carry the same amount of ATP hydrolysis energy moving into the cell, which also indicates that the kinetic energy carried by the inward Na ions is the driving force for the ATP synthesis occurring in the intracellular loop domain.

These results show that Na/K pump has a dual energy convert feature, where kinetic energy plays a significant role in converting the energy.

Figure 4A:
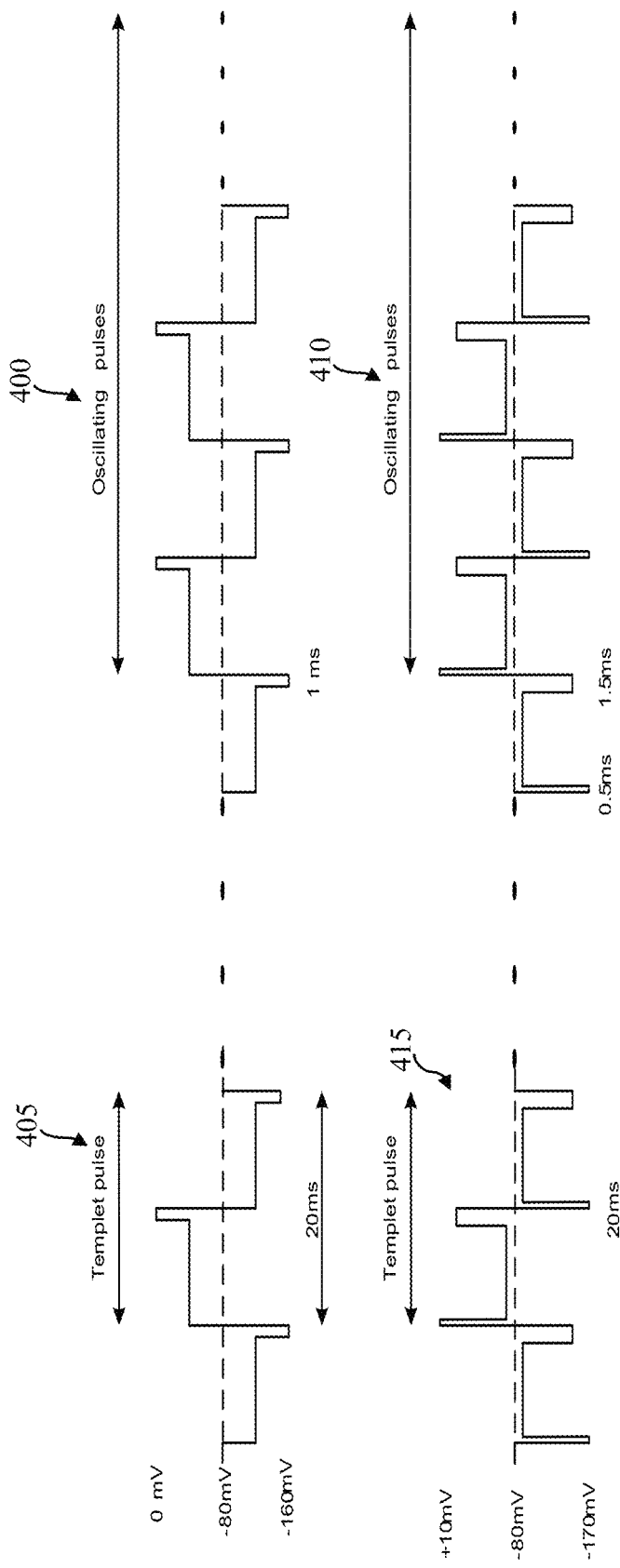
FIG. 4A illustrates the pre-pulse and oscillating pulse for both the $2^{nd}$ generation synchronization electric field synchronization electric field and the $3^{rd}$ generation synchronization electric field.
Figure 4B:
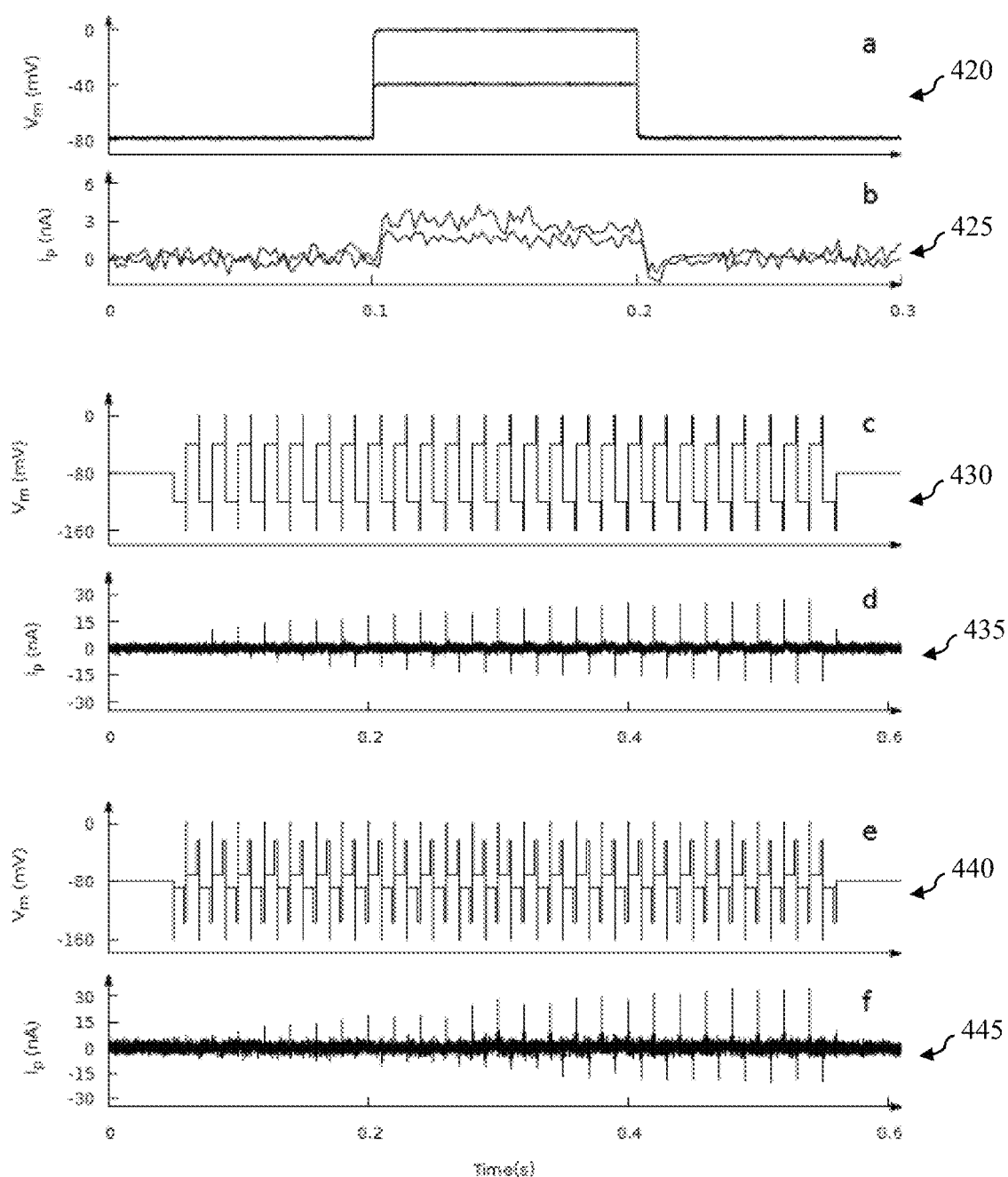
FIG. 4B illustrates the Na/K pump currents measured by the traditional single pulse, $2^{nd}$ generation synchronization electric field and $3^{rd}$ generation synchronization electric field, illustrating that after removing ATP molecules, the unchanged pump currents generated by the $3^{rd}$ generation synchronization modulation electric field prove the zero-consumption of ATP in active transporting Na and K ions.
Figure 4C:
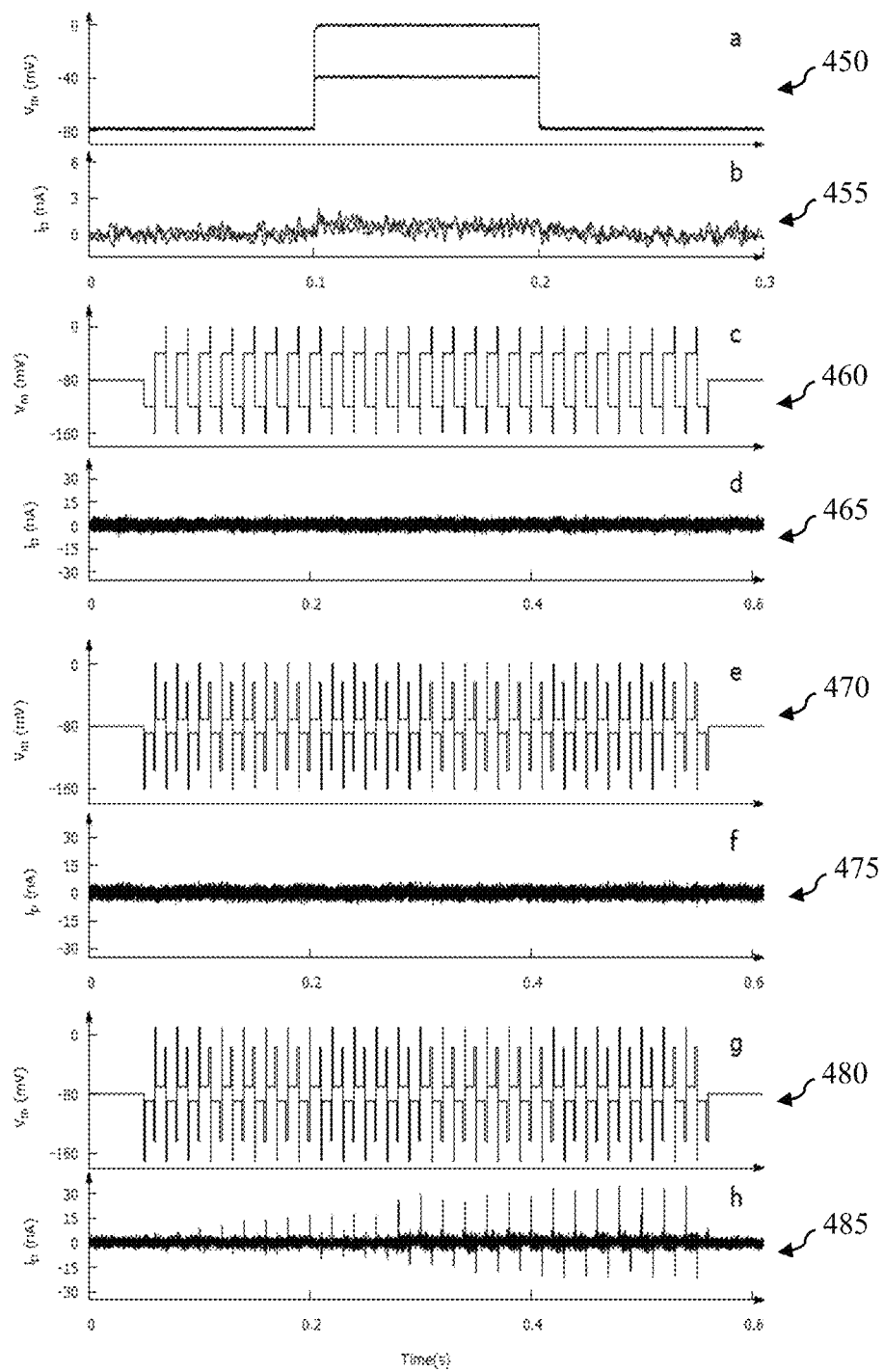
FIG. 4C illustrates the Na/K pump currents measured by the traditional single pulse, $2^{nd}$ generation synchronization electric field and $3^{rd}$ generation synchronization electric field after washing out ATP molecules.

FIG. 4A shows a single pulse of the $2^{nd}$ generation synchronization electric field 400 and the pre-pulses 405. Similarly, the $3^{rd}$ generation electric field 410 and the corresponding pre-pulses 415 are also shown in FIG. 4A. FIG. 4B and FIG. 4C illustrate, the pump currents 425, 455 generated by the respective traditional stimulation pulse 420, 450, the pump currents 435, 456 generated by the respective $2^{nd}$ generation electric field 430, 460, and the pump currents 445, 475 generated by the respective $3^{rd}$ generation electric field 440, 470, where the magnitude of the activation pulse is 80 mV. FIG. 4B represents the fields in the presence of ATP while FIG. 4C represents the fields after washing out ATP molecules. The oscillating frequency for both the $2^{nd}$ and $3^{rd}$ generation electric field is 50 Hz, which is comparable to the natural turnover rate of the pump.

From trace 425, 455, one can see that the traditional stimulation pulse-generated pump currents 425 disappeared 455 once the ATP is in washout.

Similarly, both the $2^{nd}$ generation electric field 430, 460 and the $3^{rd}$ generation electric field with the activation pulse of 80 mV 440, 470 can only generate the pump currents in the presence of ATP. Once ATP molecules are in washout, either cannot generate pump current 435, 445.

However, when the magnitude of the activation overshoot is increased to over 90 mV 480, the pump currents 485 are regenerated regardless of the low level of the ATP concentration. The value is calculated based on a dynamic model.

Figure 5A:
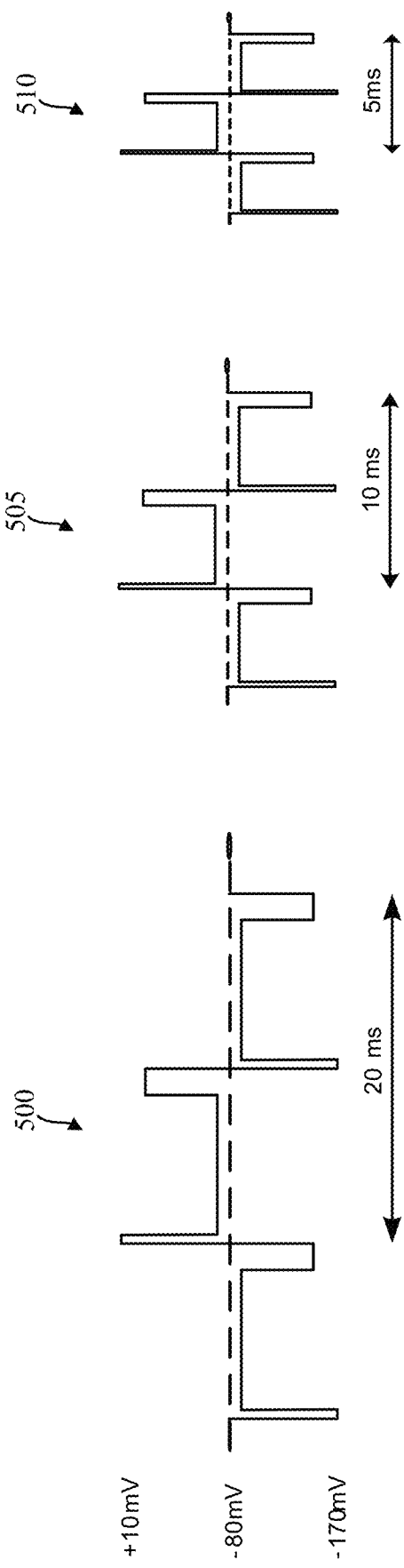
FIG. 5A illustrates the waveform of the forward modulation electric field in three phases: synchronization phase, modulation phase and maintenance phase.

FIG. 5A illustrates three phases of the oscillating electric field: synchronization phase 500 with 50 Hz frequency, modulation phase 505 where the oscillating frequency is gradually increased in a stepwise pattern (3% to 10% of the frequency change for 10 to 20 oscillating pulses) to 150 Hz, and the maintenance phase 510 where the frequency is no longer changed.

Figure 5B:
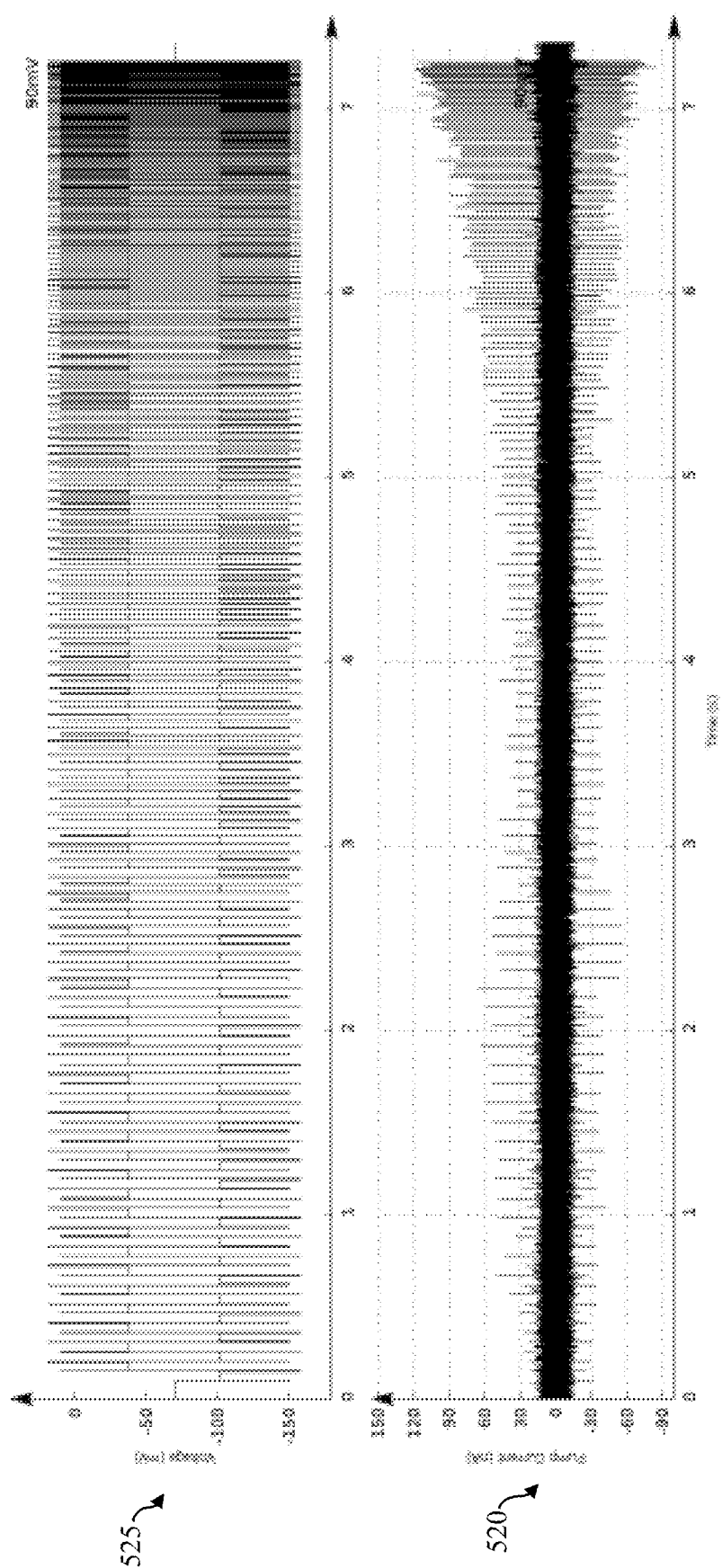
FIG. 5B illustrates the synchronized and activated Na/K pump currents in the presence of extremely low ATP concentration generated by the $3^{rd}$ forward SMEF, in accordance with the present invention.

FIG. 5B illustrates the synchronization modulation electric field 525 generated pump currents 520. As shown, not only the magnitude of the transient pump currents but also density of the pump currents (the number of transient currents per unit time) are increased.

Figure 6A:
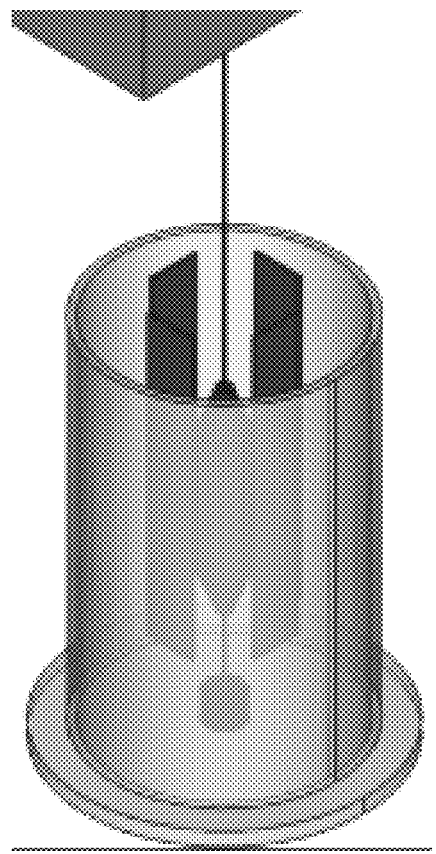
FIG. 6A illustrates an apparatus for performing muscle contraction force and multiple stimulation-induced muscle fatigue.
Figure 6B:
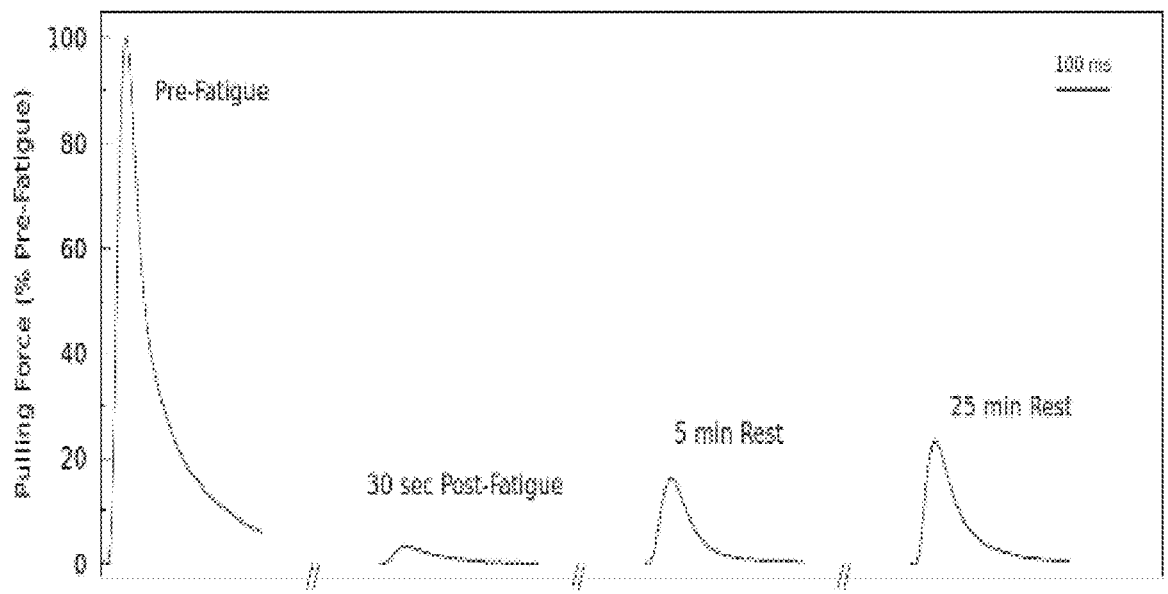
FIG. 6B illustrates the work-induced muscle fatigue established by the apparatus of FIG. 6A.

FIG. 6A-FIG. 6B illustrate a method for the measurement of the muscle contraction force and the multiple stimulation-induced muscle fatigue. A single twitch muscle fiber, Semitendinosus, from a bullfrog was positioned in a custom-made chamber with a sensor for contraction force as shown in FIG. 6A. Electric stimulations are provided through the innervated nerves.

Figure 6C:
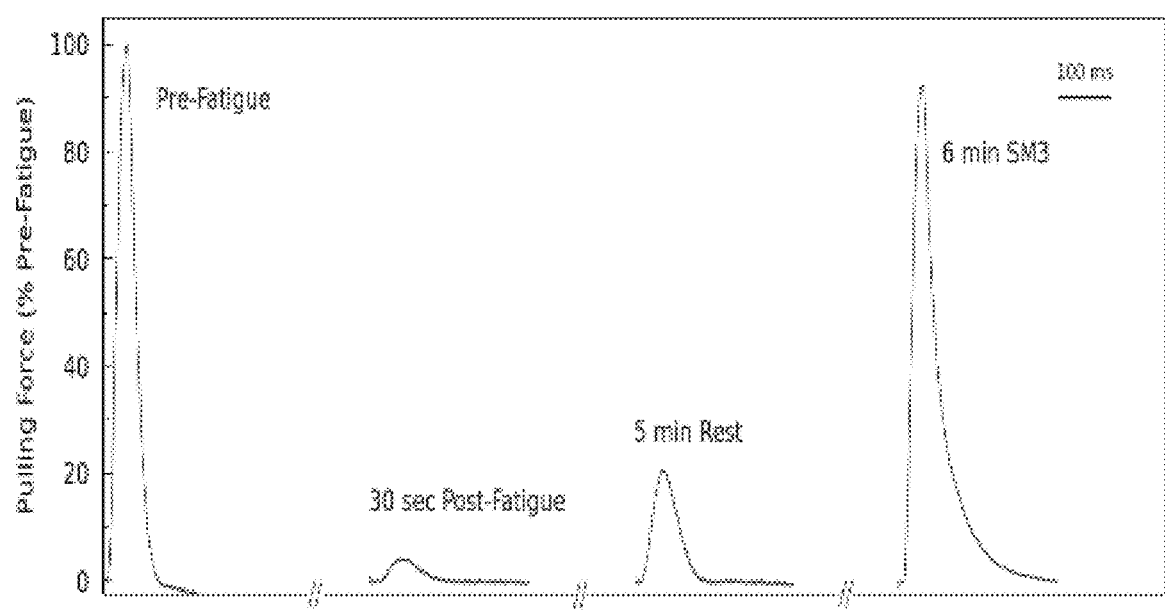
FIG. 6C illustrates how the $3^{rd}$ SMEF can effectively reduce the extensive work-induced muscle fatigue established by the apparatus of FIG. 6A.

The muscle was first fatigued by 600 nerve stimulations and then allowed to rest. After initial 5 minutes recovery, 25 more minutes of rest only allowed the muscles to recover to 25% as shown in FIG. 6B. In contrast, 6 more minutes application of the 3rd SMEF can allow for almost fully recover to 90% as shown in FIG. 6C. As shown, application of the 3rd SMEF can significantly recover the contraction force.

Figure 7A:
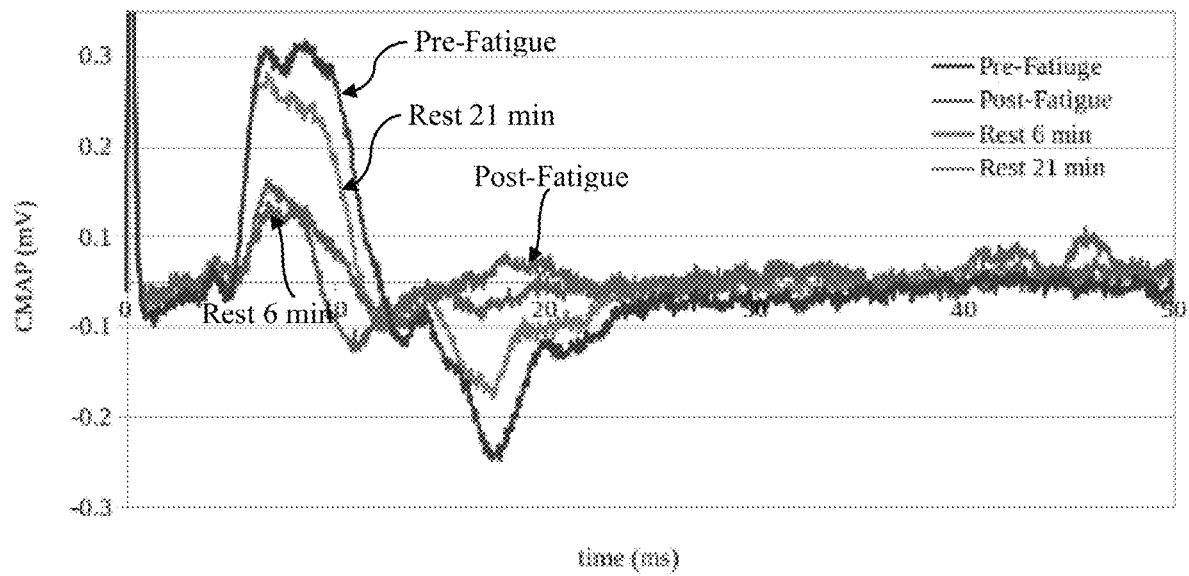
FIG. 7A illustrates compound muscle action potential recovery of the maximum voluntary force (MVF) of the skeletal muscles of human beings without stimulation.
Figure 7B:
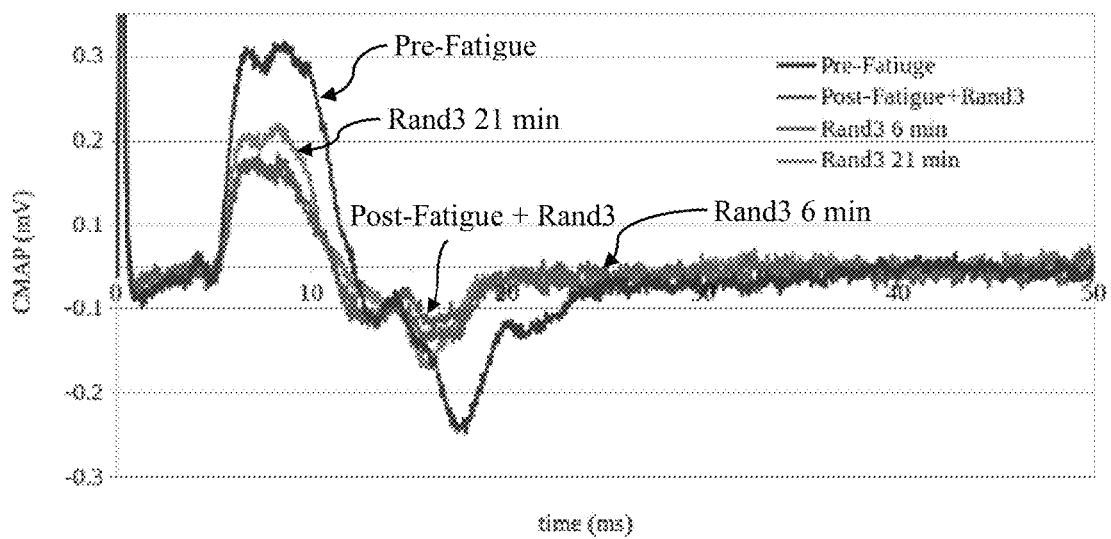
FIG. 7B illustrates compound muscle action potential recovery of the maximum voluntary force (MVF) of the skeletal muscles of human beings with Rand3 stimulation.
Figure 7C:
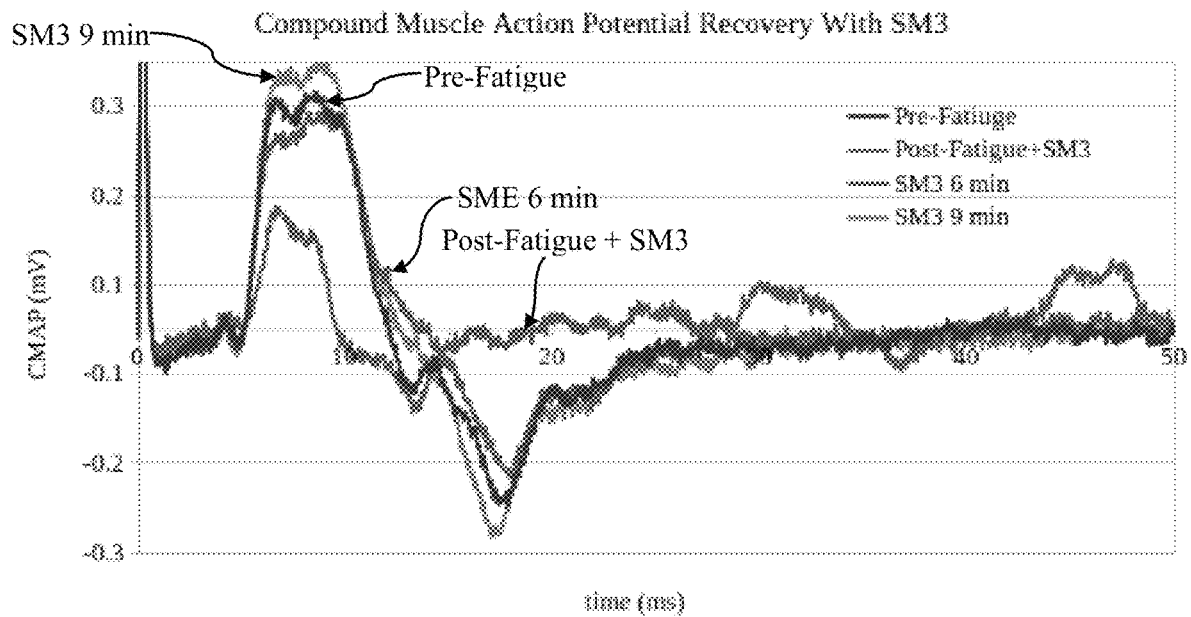
FIG. 7C illustrates compound muscle action potential recovery of the maximum voluntary force (MVF) of the skeletal muscles of human beings with $3^{rd}$ SMEF stimulation.
Figure 7D:
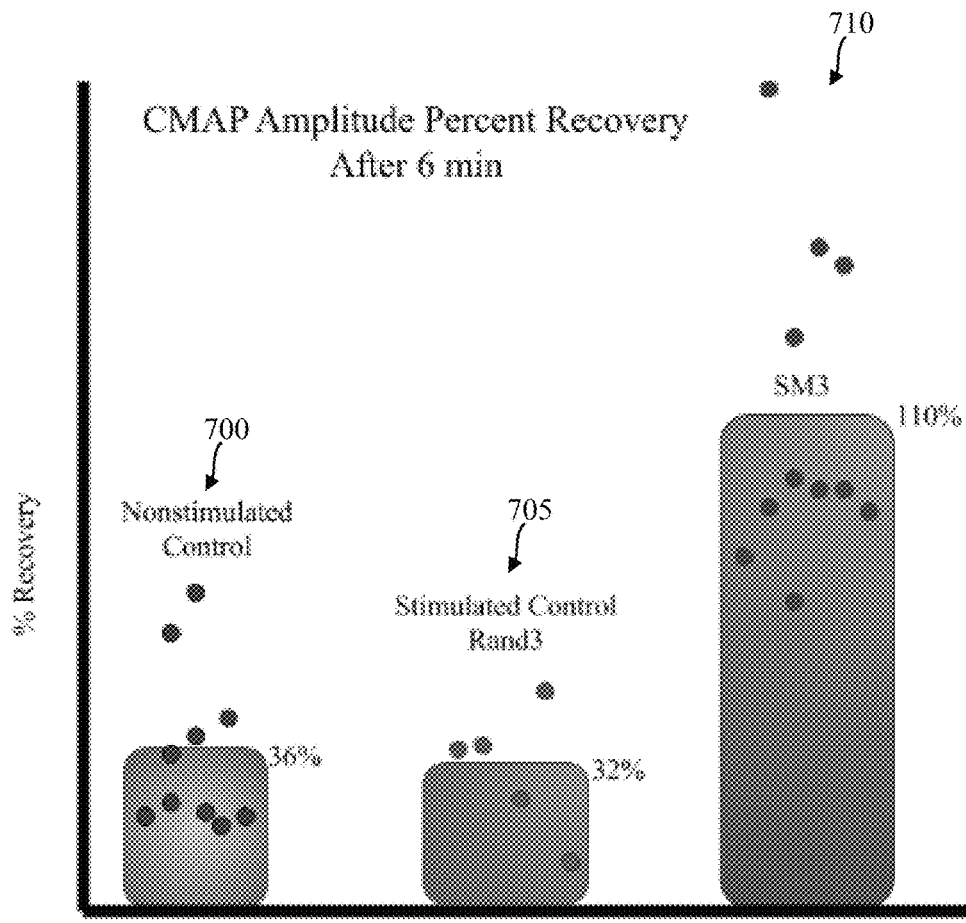
FIG. 7D summarizes the results of FIG. 7A-FIG. 7C.

FIG. 7A-FIG. 7D illustrate how the 3rd SMEF can facilitate recovery of the muscle fatigue by study of the maximum voluntary force (MVF) of a human being. Recovery of the compound muscle action potential (CMAP) has commonly served as a marker for the muscle recovery from fatigue. FIG. 7D compares the recovery of the CMAP on the exercising forearm muscles of six volunteers in the age from 22 to 25. For control groups without stimulation as shown in FIG. 7A, or with random frequency as shown in FIG. 7B, 6 minutes of rest only recovered the CMAP for average of 36%, while 6 minutes of the application of the 3rd SMEF, as shown in FIG. 7C, fully recovered the CMAP (110%).

The CMAP recovery is illustrated without any stimulation, as shown in FIG. 7A, with random frequency, as shown in FIG. 7B, or with the 3rd SMEF, as shown in FIG. 7C. FIG. 7D summarizes the recovery of the CMAP, wherein the nonstimulated control 700 represents the recovery without any stimulation (Range: 21-71%, ave=36%, stdev=18%, n=10). The stimulated control Rand3 705 represents the recovery with the random frequency of the $3^{rd}$ SMEF (Range: 11-49%, ave=32%, stdev=14%, n=5). The blue SM3 710 represents the recovery with the $3^{rd}$ SMEF (Range: 69-183%, ave=110%, stdev=35%, n=11).

Figure 8:
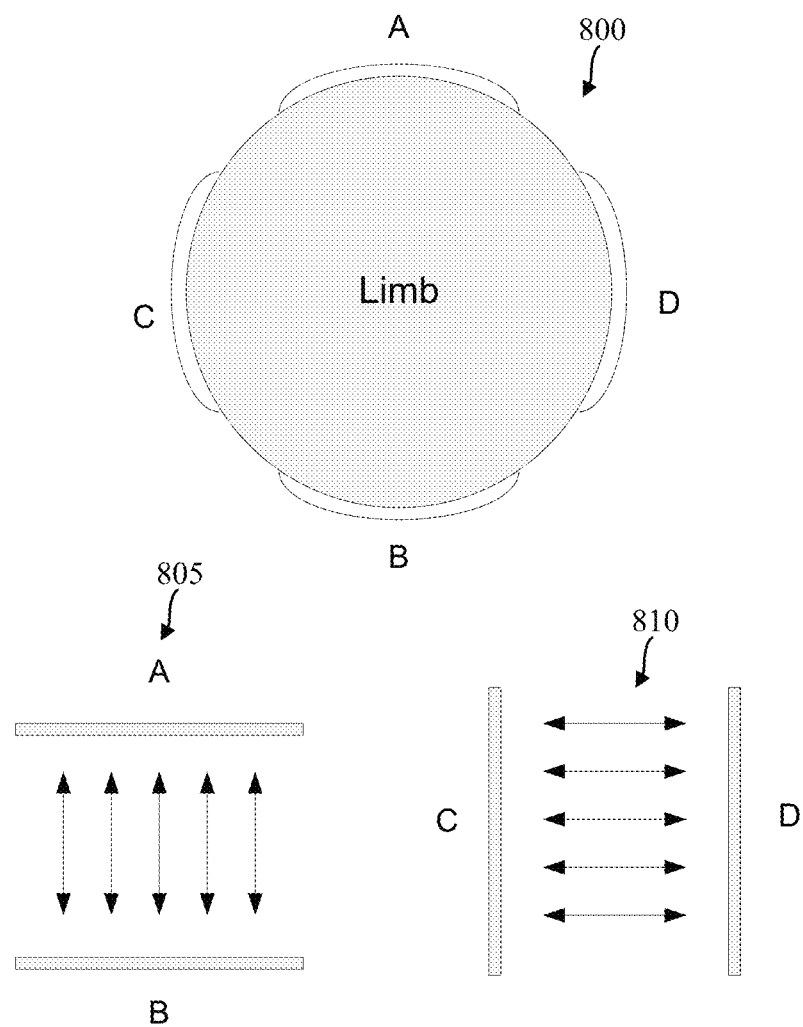
FIG. 8 illustrates the electrodes to apply the $3^{rd}$ generation synchronization modulation electric field to an ischemia limb.

FIG. 8 illustrates the application of the $3^{rd}$ SMEF to ischemia limb by the two-dimensional electrodes. Na/K pumps are known to be widely distributed in muscle fibers of limbs. From physics, when the cell membrane is perpendicular to the applied electric field, the Na/K pumps on the surface can experience the field-induced membrane potential. To maximally activate the pump molecules in limb, the electric field through 2-dimension electrodes was applied.

As shown, the cross section of is shown 800, two pair (AB and CD) of electrodes are perpendicularly placed along the limb. One pair of the electrodes (AB) is vertically applied crossing the limb while another pair of the electrodes (CD) is horizontally applied crossing the limb.

Two identical $3^{rd}$ generation synchronization modulation electric fields are simultaneously applied to the ischemia limbs through the two pairs of electrodes. To maximally influence the Na/K pumps in different orientations, two pairs of electrodes cannot touch each other. Two electric fields must be independent, without common ground, but have exactly the same waveform, without any time-delay of shift. In other words, two independent signal generators must be triggered by the same signal.

In the embodiment illustrated in FIG. 8, the electric field is vertically applied 805 to the ischemia limb 800, and the electric field is also horizontally applied 810 to the ischemia limb 800.

Figure 9:
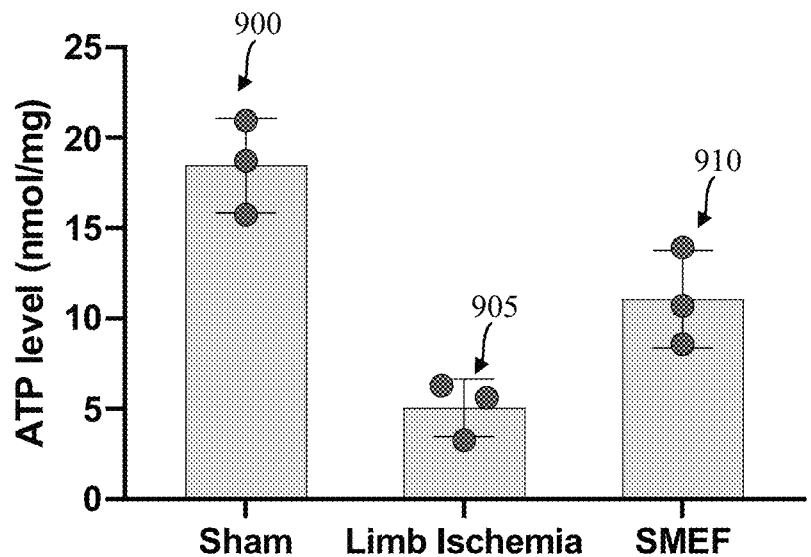
FIG. 9 illustrates the effects of the $3^{rd}$-SMEF on ATP concentration in skeletal muscle during ischemia.

FIG. 9 illustrates the effects of the $3^{rd}$-SMEF on ATP concentration in skeletal muscle during ischemia. To demonstrate if the $3^{rd}$-SMEF can be applied on the hindlimb to protect against IRI, preliminary studies were performed in SD male rats (10-12 w). For the experiment, surgical procedures were used to clamp the aorta of the rat to the limb for 60 minutes, and the $3^{rd}$-SMEF was simultaneously applied to one hindlimb during ischemia with forward modulation at 1V (SMEF group) 910. The other hindlimb, without application of the electric field was taken as an ischemic control (ischemia group) 905. The rats operated using the same surgical procedure, but without aorta clamping and SMEF application, were taken as a sham group 900. Samples were collected at 60 min after clamping.

As illustrated in FIG. 9, the ATP level was decreased by ~72% in limb ischemic group 905 but only by ~40% in the $3^{rd}$-SMEF treated group 910 compared with sham group 900. Application of the $3^{rd}$-SMEF preserved ATP about >50% compared with the ischemic group without application of the electric field. These results show that 1) the $3^{rd}$-SMEF can be effectively applied on hindlimbs; and 2) application of the $3^{rd}$-SMEF preserves ATP concentration during ischemia.

Figure 10:
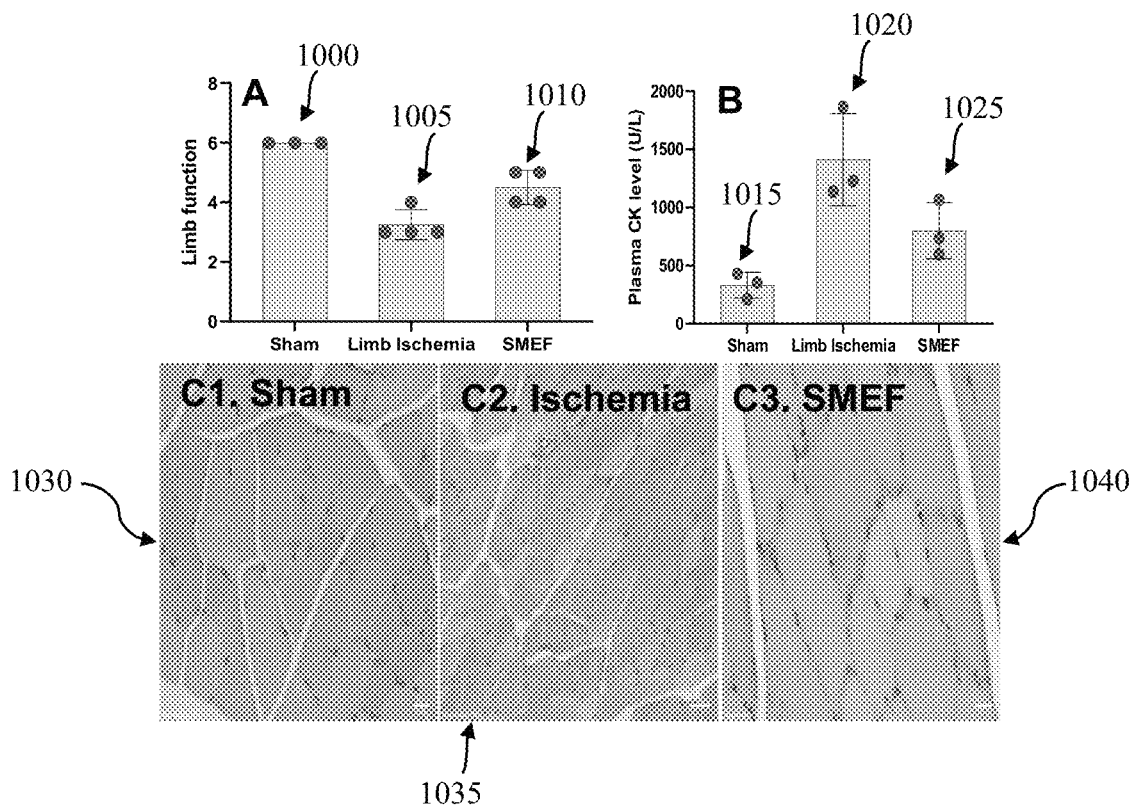
FIG. 10 illustrates the effects of the $3^{rd}$-SMEF on functional recovery and injuries of the hindlimbs after IRI.

FIG. 10 illustrates the effects of the $3^{rd}$-SMEF on functional recovery from injuries of the hindlimbs after IRI (ischemia-reperfusion injury). To determine if the $3^{rd}$-SMEF protects against the IRI and improves the limb functional recovery, preliminary studies were performed in SD male rats (10-12 w). Surgical procedures were the same as described above with reference to FIG. 9. Clamping time was 60 min. The $3^{rd}$-SMEF was applied on one hindlimb during ischemia with forward modulation at 1V (SMEF group). The other hindlimb without application of the SMEF was taken as an ischemic control (ischemia group). The rats operated on using the same surgical procedures but without aorta clamping or SMEF application were taken as a sham group. At the end of ischemia, the clips were released, the electrodes were removed, wounds were closed, and the animals were allowed to recover. At 24 hours after IRI, limb function, CK levels, and histology were evaluated.

FIG. 10 shows that the application of the $3^{rd}$-SMEF improved functional recovery of the hindlimbs. Limb function was assessed with Tarlov scale. As shown in FIG. 10, application of the $3^{rd}$-SMEF improved the limb function recovery by >40% 1010 compared with the ischemia group without using the electric field 1005 compared with the sham group 1000.

FIG. 10 also shows that the application of the $3^{rd}$-SMEF reduced CK level. In particular, the CK level increased by ~3-folds in limb ischemia group 1020 but only by ~1.8-folds in SMEF group 1025 compared with the sham group 1015.

FIG. 10 additionally shows that the application of the $3^{rd}$-SMEF decreased skeletal muscle injury in histology. In particular, histology of skeletal muscle with PAS staining showed a more severe injury in the ischemia group, including the reduced size of fibers, disordered arrangement, and focal necrosis (loss of nuclei in some fibers) 1035, compared with the $3^{rd}$-SMEF-treated group 1040 and the sham group 1030.

These preliminary data indicate that application of the $3^{rd}$-SMEF protected against IRI and improved functional recovery of the hindlimbs.

Based on these and other studies, a dynamic model of the Na/K pump can be expressed as follows: ATP hydrolysis energy is converted to the kinetic energy of inorganic Pi directly drive 3 Na ions out of the cell. Na ions carry the ATP hydrolysis energy as the kinetic energy freely and quickly moving along a channel-like structure against the electrochemical potential difference. At end of the channel, the kinetical energy left on 3 Na ions is transferred at the loop domain to the K-transport driving 2 K into the cell along the channel. Since K and Na ions move in the opposite direction across the cell membrane, the inward K ions may gain energy from the membrane potential. Similarly, any energy remaining on the K ions is transferred to the Na-transport to compensate for any energy deficiency in Na-transport. As a result, kinetic energy plays a significant role throughout the loop of the pumping cycle.

In addition to the normal physiological running mode consuming ATP to actively transport Na and K ions, Na/K pump have several non-canonical modes, such as K-K exchange mode and Na/Na exchange mode where the same amount ions are transported across the cell membrane without ATP consumption. Briefly, in the first half-cycle, ATP hydrolysis energy drives Na ions out of the cell to build up potential energy difference, while in the next half-cycle, the Na potential energy drives the extracellular Na ions downhill into the cell, where the kinetic energy carried by the inward Na ions is the energy source for the ATP synthesis.

The synchronized pump currents at the Na/Na exchange mode showed transient outward and inward pump current with the same magnitude and duration. The results indicate that similar to the ATP driving Na ions freely and kinetically out of the cell, the same amount of extracellular Na ions quickly move into the cell, freely and kinetically, where the potential energy is converted to the kinetic energy of ions to synthesize ATP molecules. This is similar to the ATP synthesizers, such as bacteriorhodopsin and F0F1-ATPases, proton potential energy is transformed to the mechanical energy of the down-stream protons to rotate the F0 domain in F0F1 ATPase to synthesize ATP.

The strategy in the development of the $3^{rd}$ generation synchronization modulation is to utilize the dual energy conversion features by combining the intrinsic mechanisms of Na/K pumps involved in normal pumping mode and non-canonical model, and by introducing the concept of the electronic synchrotron accelerator to the biological system. Initially, pump molecules are synchronized to the physiological running mode consuming ATP to drive 3 Na and 2 K ions. Simultaneously, the electric field is used to accelerate the ion-movements to inject energy to the pump molecules. At the end of the pumping cycle, the pumping cycle is switched to the non-canonical mode so that the kinetic energy carried by the 2 K ions is transferred to the Pi by kicking out it into the solution. Due to the large molecular weight of nucleotide having diffusion constant 3 orders less than ions, the ADP molecules released at the beginning of the pumping cycle cannot move far away. When Pi carrying high kinetical energy hits the ADP, they form the ADP. As a result, the Na/K pumps on one hand, consume ATP to transport Na and K ions to build up ionic concentration gradients and the membrane potential difference, and on the other, using the injected electric energy of the ions to synthesize ATP. As a result, the net ATP-consumption will be significantly reduced, theoretically to zero.

The $3^{rd}$ generation synchronization modulation technique provides a method or a process to electrically fuel Na/K pumps and control the turnover rate of the pumping cycle to a pre-determined value with less or zero consumption of ATP.

Each half-cycle of the oscillating electric field consists of three sections, the short activation overshoot electric pulse, energy trap overshot electric pulse and a plateau in between with a wide duration and low magnitude. Once two ion-transports are entrapped into the corresponding favorite half-cycles, the positive and negative plateaus will activate the Na- and K-transports, respectively, to push the steps of ion-movements or the Na- and K-pump currents towards to the front of the corresponding half-pulses, respectively in the corresponding half-pulses. Once falling into the front un-favorite half-pulse, the ion-transports will be inhibited until the pulses change their polarity. Therefore, the Na and K pump currents will be restricted into the activation overshoot of the beginning of the favorite half-pulses, respectively. In other words, the step of the Na and K ion-movements in the channel-like structures from all the pump molecules are synchronized.

Duration and magnitude of two overshoot electric pulses and the plateau are designed based on the functions of Na/K pumps. For the energy-trap overshoot pulse, it must have high enough magnitude to block the un-favorite ion-transport. Duration will be dependent on how fast the pump molecules are to be synchronized. The wider the energy-trap overshoot pulse, the faster the pump molecules can be synchronized, or the fewer oscillating pulses are required to synchronize the pump molecules. However, the wider the overshoot pulse, the higher the chance to influence the functions of other voltage-dependent membrane proteins. Duration of the activation overshoot pulse is short, only a few hundred microseconds long enough to cover the pump currents. Magnitude is calculated based on the mechanisms involved in the ATP synthesis and the minimal energy required to synthesize ATP molecule.

Duration of the pump currents will reflect characteristics of the ion-movements in the pump molecules. The transient pump currents for both outward Na- and inward K-currents with the extremely short time course, as short as the membrane capacitance currents, proving that the free and kinetic movements of the ions along a channel-like structure without the protein conformational change involved. Consequently, the activation overshoot pulse at the beginning of each of the half-pulse is designed to accelerate the ion-movements for injecting electric energy to the pump molecules.

The $3^{rd}$ SMEF of the present invention consists of three phases, Phase 1 is to synchronize the pump molecules down to the individual steps throughout the pumping cycle consuming one ATP to actively transport 3 Na and 2 K ions and injecting enough electric energy to the pump molecules in order to synthesize one ATP at the end of the pumping cycle. Phase 2 is to modulate the pumping rate of the synchronized pump molecules to a pre-determined target value by gradually changing the synchronization frequency in a step wise pattern. Phase 3 is to maintain the pumping rate at the target value for a certain period, based on the clinical requirement.

The $3^{rd}$-SMEF has been specifically designed to avoid side effects on the cell membrane and other membrane proteins. For example, to avoid interrupting the integrity of the cell membrane and the membrane proteins, the field-induced membrane potentials are all in physiological range, much lower than the thresholds of membrane electroporation and protein denature. Short duration of the overshoot pulses (only a few hundred µs) is not long enough to open the voltage-gated ion channels, including the Na-channels having the fastest electric response. The oscillating waveform of the $3^{rd}$ SMEF was specifically designed for Na/K pumps, transporting two kinds of cations in the opposite direction, and 50 Hz frequency is comparable to the natural turnover rate of Na/K pumps which is far away from other pumps, such as Ca2+ pump of 500 Hz.

The present invention provides a well-designed electrode array for application of the $3^{rd}$ generation synchronization modulation electric field specifically to the ischemia limb. Because the electric field only positioned perpendicular to the cell membrane can affect the pump molecules, and orientation of muscle fibers along the limb, a two-dimensional electrode is designed to maximally activate the pump molecules.

The present invention may be embodied on various computing platforms that perform actions responsive to software-based instructions and most particularly on touchscreen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. However, as indicated above, due to circuit statutory subject matter restrictions, claims to this invention as a software product are those embodied in a non-transitory software medium such as a computer hard drive, flash-RAM, optical disk or the like.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object-oriented programming language such as Java, C#, C++, Visual Basic or the like and conventional procedural programming languages, such as the "C" programming language or similar programming languages.

It should be emphasized that the above-described embodiments of the present disclosure are merely possible examples of implementations set forth for a clear understanding of the principles of the disclosure. Many variations and modifications can be made to the above-described embodiment(s) without departing substantially from the spirit and principles of the disclosure. All such modifications and variations are intended to be included herein within the scope of this disclosure and protected by the following claims.

What is claimed is:

1. A method for controlling Na/K pump molecules for the treatment of limb ischemia, the method comprising:
    applying an oscillating electric field to an ischemia limb comprising Na/K pump molecules, wherein the oscillating electric field comprises three serially applied phases and wherein applying the oscillating electric field comprises;
        applying a synchronization phase to synchronize the Na/K pump molecules down to individual steps within a running cycle at an Na/K pump molecule physiological turnover rate with a net-consumption of adenosine triphosphate (ATP) substantially equal to zero;
        applying a modulation phase to up modulate the synchronized Na/K pump molecules to a predetermined target turnover rate; and
        applying a maintenance phase to maintain the synchronized Na/K pump molecules at the predetermined target turnover rate for a predetermined duration of time.

2. The method of claim 1, wherein the oscillating electric field comprises a positive half-cycle resulting in an extrusion of 3 Na ion and a negative half-cycle resulting in a pumping-in of 2 K ions.

3. The method of claim 2, wherein the oscillating electric field further comprises:
    a positive activation overshoot electric pulse at a start of the positive half-cycle;
    a positive energy-trap overshoot electric pulse at an end of the positive half-cycle;
    a negative activation overshoot electric pulse at a start of the negative half-cycle; and
    a negative energy-trap overshoot electric pulse at an end of the negative half-cycle.

4. The method of claim 3, wherein an outward Na current is restricted at the start of the positive activation overshoot electric pulse in the positive half-cycle and the positive activation overshoot electric pulse activates an Na-movement to inject electric energy to the Na ions, and wherein an inward K current is restricted at the start of the negative activation overshoot electric pulse in the negative half-cycle and the negative activation overshoot electric pulse accelerates a K-movement to inject electric energy to the K ions to synthesize one ATP molecule.

5. The method of claim 4, wherein the one synthesized ATP molecule compensates for ATP consumed during the extrusion of 3 Na ions and pumping-in of 2 K ions, resulting in the net-consumption of adenosine triphosphate (ATP) substantially equal to zero.

6. The method of claim 3, wherein a magnitude of the positive activation overshoot electric pulse is selected to allow the Na/K pumps to operate within a physiological range of the membrane potentials of the ischemia limb and a magnitude of the negative activation overshoot electric pulse is selected to allow the Na/K pumps to operate within a physiological range of the membrane potentials of the ischemia limb.

7. The method of claim 3, wherein a magnitude of the positive energy-trap overshoot electric pulse is selected to allow the Na/K pumps to operate within the physiological range of the membrane potentials of the ischemia limb and a magnitude of the negative energy-trap overshoot electric pulse is selected to allow the Na/K pumps to operate within the physiological range of the membrane potentials of the ischemia limb.

8. The method of claim 3, wherein a duration of the positive activation overshoot electric pulse is about 300 us or less and a duration of the negative activation overshoot electric pulse is about 300 us or less.

9. The method of claim 3, wherein a magnitude of the positive activation overshoot electric pulse is at least about 95 mV and a magnitude of the negative activation overshoot electric pulses is at least about 95 mV.

10. The method of claim 3, wherein a duration of the positive energy-trap overshoot electric pulse is about 400 us or less and a duration of the negative energy-trap overshoot electric pulses is about 400 us or less.

11. The method of claim 3, wherein a magnitude of the positive energy-trap overshoot electric pulse is about 60 mV and a magnitude of the negative energy-trap overshoot electric pulses is about 60 mV.

12. The method of claim 3, wherein the synchronization phase further comprises an electric field plateau between the positive activation overshoot electric pulse and the positive energy-trap overshoot electric pulse and wherein a magnitude of the electric field plateau between the positive activation overshoot electric pulse and the positive energy-trap overshoot electric pulse is about 30 mV.

13. The method of claim 3, wherein the synchronization phase further comprises an electric field plateau between the negative activation overshoot electric pulse and the negative energy-trap overshoot electric pulse and wherein a magnitude of the electric field plateau between the negative activation overshoot electric pulse and the negative energy-trap overshoot electric pulse is about 30 mV.

14. The method of claim 1, wherein a frequency of the oscillating electric field during the application of the synchronization phase is about 50 Hz.

15. The method of claim 3, wherein the modulation phase further comprises an electric field plateau between the negative activation overshoot electric pulse and the negative energy-trap overshoot electric pulse and wherein a duration of the electric field plateau is reduced during the modulation phase.

16. The method of claim 1, wherein a frequency of the oscillating electric field during the modulation phase is gradually increased to accelerate the pumping rate to the pre-determined target turnover rate.

17. The method of claim 16, wherein the frequency of the oscillating electric field during the modulation phase is gradually increased by about 10% for each 10 oscillating pulses of the oscillating electric field having the same frequency.

18. The method of claim 1, where the oscillating electric field is applied to a surface of the ischemia limb using a first pair of electrodes and the oscillating electric field is applied to the surface of the ischemia limb using a second pair of electrodes, wherein the first pair of electrodes and the second pair of electrodes are positioned perpendicular to each other on the surface of the ischemia limb and wherein the first pair of electrodes and the second pair of electrodes are independent and wherein the oscillating electric field applied by the first pair of electrodes and the oscillating electric field applied by the second pair of electrodes are the same oscillating electric field and are applied simultaneously.

19. A system for controlling Na/K pump molecules for the treatment of limb ischemia, the system comprising:
   an electric field generator to generate an oscillating electric field;
   a first pair of electrodes and a second pair of electrodes to simultaneously apply the oscillating electric field to an ischemia limb comprising Na/K pump molecules, wherein the first pair of electrodes and the second pair of electrodes are positioned perpendicular to each other on the surface of the ischemia limb, wherein the first pair of electrodes and the second pair of electrodes are independent and wherein the oscillating electric field comprises three serially applied phases and applying the oscillating electric field comprises;
      applying a synchronization phase to synchronize the Na/K pump molecules down to individual steps within a running cycle at an Na/K pump molecule physiological turnover rate with a net-consumption of adenosine triphosphate (ATP) substantially equal to zero;
      applying a modulation phase to up modulate the synchronized Na/K pump molecules to a predetermined target turnover rate; and
      applying a maintenance phase to maintain the synchronized Na/K pump molecules at the predetermined target turnover rate for a predetermined duration of time.

20. A non-transitory storing a set of instructions configured for being executed by at least one processor for performing a method for controlling Na/K pump molecules for the treatment of limb ischemia, the method comprising:
   controlling an electric field generator to apply an oscillating electric field to an ischemia limb comprising Na/K pump molecules, wherein the oscillating electric field comprises three serially applied phases and wherein applying the oscillating electric field comprises;
      applying a synchronization phase to synchronize the Na/K pump molecules down to individual steps within a running cycle at an Na/K pump molecule physiological turnover rate with a net-consumption of adenosine triphosphate (ATP) substantially equal to zero;
      applying a modulation phase to up modulate the synchronized Na/K pump molecules to a predetermined target turnover rate; and
      applying a maintenance phase to maintain the synchronized Na/K pump molecules at the predetermined target turnover rate for a predetermined duration of time.

* * * * *